(12) United States Patent
Jensen et al.

(10) Patent No.: US 10,265,691 B2
(45) Date of Patent: Apr. 23, 2019

(54) OLEFIN METATHESIS CATALYSTS

(71) Applicant: Bergen Teknologioverforing AS, Bergen (NO)

(72) Inventors: Vidar R. Jensen, Bergen (NO); Giovanni Occhipinti, Kleppesto (NO)

(73) Assignee: Bergen Teknologioverforing AS, Bergen (NO)

( * ) Notice: Subject to any disclaimer, the term of this patent is extended or adjusted under 35 U.S.C. 154(b) by 0 days.

(21) Appl. No.: 15/742,668

(22) PCT Filed: Jul. 8, 2016

(86) PCT No.: PCT/EP2016/066286
§ 371 (c)(1),
(2) Date: Jan. 8, 2018

(87) PCT Pub. No.: WO2017/009232
PCT Pub. Date: Jan. 19, 2017

(65) Prior Publication Data
US 2018/0200704 A1 Jul. 19, 2018

(30) Foreign Application Priority Data

Jul. 10, 2015 (EP) .................................... 15176276

(51) Int. Cl.
| | | |
|---|---|---|
| B01J 31/22 | (2006.01) | |
| C07F 15/00 | (2006.01) | |
| C07C 2/02 | (2006.01) | |
| C07D 313/00 | (2006.01) | |
| B01J 31/18 | (2006.01) | |

(52) U.S. Cl.
CPC ......... *B01J 31/2278* (2013.01); *B01J 31/181* (2013.01); *B01J 31/226* (2013.01); *C07C 2/02* (2013.01); *C07D 313/00* (2013.01); *C07F 15/0046* (2013.01); *B01J 2231/20* (2013.01); *B01J 2231/324* (2013.01); *B01J 2231/543* (2013.01); *B01J 2531/821* (2013.01)

(58) Field of Classification Search
CPC ............ B01J 31/2269; B01J 2231/324; C07F 15/0046
See application file for complete search history.

(56) References Cited

U.S. PATENT DOCUMENTS

| 8,716,488 B2 | 5/2014 | Jensen et al. |
| 9,303,100 B2 | 4/2016 | Jensen et al. |
| 2015/0025212 A1 | 1/2015 | Jensen et al. |

FOREIGN PATENT DOCUMENTS

| EP | 2826783 A1 | 1/2015 |
| WO | WO 2004/112951 A2 | 12/2004 |
| WO | WO 2005/012315 A1 | 2/2005 |
| WO | WO2005012315 | * 2/2005 |
| WO | WO 2012/032131 A1 | 3/2012 |

OTHER PUBLICATIONS

Extended European Search Report dated Oct. 30, 2015 for Application No. EP 15176276.2.
International Search Report and Written Opinion dated Aug. 16, 2016 for Application No. PCT/EP2016/066286.
EP 15176276.2, dated Oct. 30, 2015, Extended European Search Report.
PCT/EP2016/066286, dated Aug. 16, 2016, International Search Report and Written Opinion.
U.S. Appl. No. 13/626,449, filed Sep. 25, 2012, Jensen et al.
U.S. Appl. No. 14/269,007, filed May 2, 2014, Jensen et al.
U.S. Appl. No. 14/334,302, filed Jul. 17, 2014, Jensen et al.
U.S. Appl. No. 15/087,413, filed Mar. 31, 2016, Jensen et al.
EP 14177478.6, dated Dec. 18, 2014, Extended European Search Report and European Search Opinion.
PCT/EP2011/065586, dated Dec. 30, 2011, International Search Report and Written Opinion.
Extended European Search Report and European Search Opinion dated Dec. 18, 2014 in connection with EP14177478.6.
International Search Report and Written Opinion dated Dec. 30, 2011 in connection with PCT/EP2011/065586.
Kotyk et al., Geometric and Electronic Structure of a C1-Symmetric Ruthenium-Aryloxide Metathesis Catalyst: An Experimental and Computational Study. Organometallics. Sep. 28, 2009;28(18):5424-5431, XP002638065, doi: 10.1021/om900429n. Epub Aug. 24, 2009.
Occhipinti et al., Theory-assisted development of a robust and Z-selective olefin metathesis catalyst. Dalton Trans. Aug. 7, 2014;43(29):11106-17. doi: 10.1039/c4dt00409d. Epub Apr. 30, 2014.
Tanaka et al., Anionic Ligand Exchange in Hoveyda-Grubbs Ruthenium(II) Benzylidenes. Organometallics. 2006; 25(24):5696-5698. doi: 10.1021/om060913n. Epub Oct. 18, 2016.
Torker et al., The influence of anionic ligands on stereoisomerism of Ru carbenes and their importance to efficiency and selectivity of catalytic olefin metathesis reactions. J Am Chem Soc. Mar. 5, 2014;136(9):3439-55. doi: 10.1021/ja410606b. Epub Feb. 17, 2014.
Torker et al., Tuning the Steric Properties of a Metathesis Catalyst for Copolymerization of Norbornene and Cyclooctene toward Complete Alternation. Organometallics. Jun. 28, 2010;29(12):2735-2751. doi: 10.1021/om100185g. Epub Jun. 3, 2010.

* cited by examiner

*Primary Examiner* — Rebecca L Anderson
*Assistant Examiner* — Karen Cheng
(74) *Attorney, Agent, or Firm* — Wolf, Greenfield & Sacks, P.C.

(57) ABSTRACT

The present invention refers to novel ruthenium-based catalysts for olefin metathesis reactions, particularly to fast initiating catalysts having stereoselective properties. In olefin metathesis reactions, the disclosed catalysts provide a high catalytic activity combined with the capability to generate higher yields of the olefin metathesis product.

19 Claims, 3 Drawing Sheets

OLEFIN METATHESIS CATALYSTS

CROSS REFERENCE TO RELATED APPLICATIONS

Figure 1:
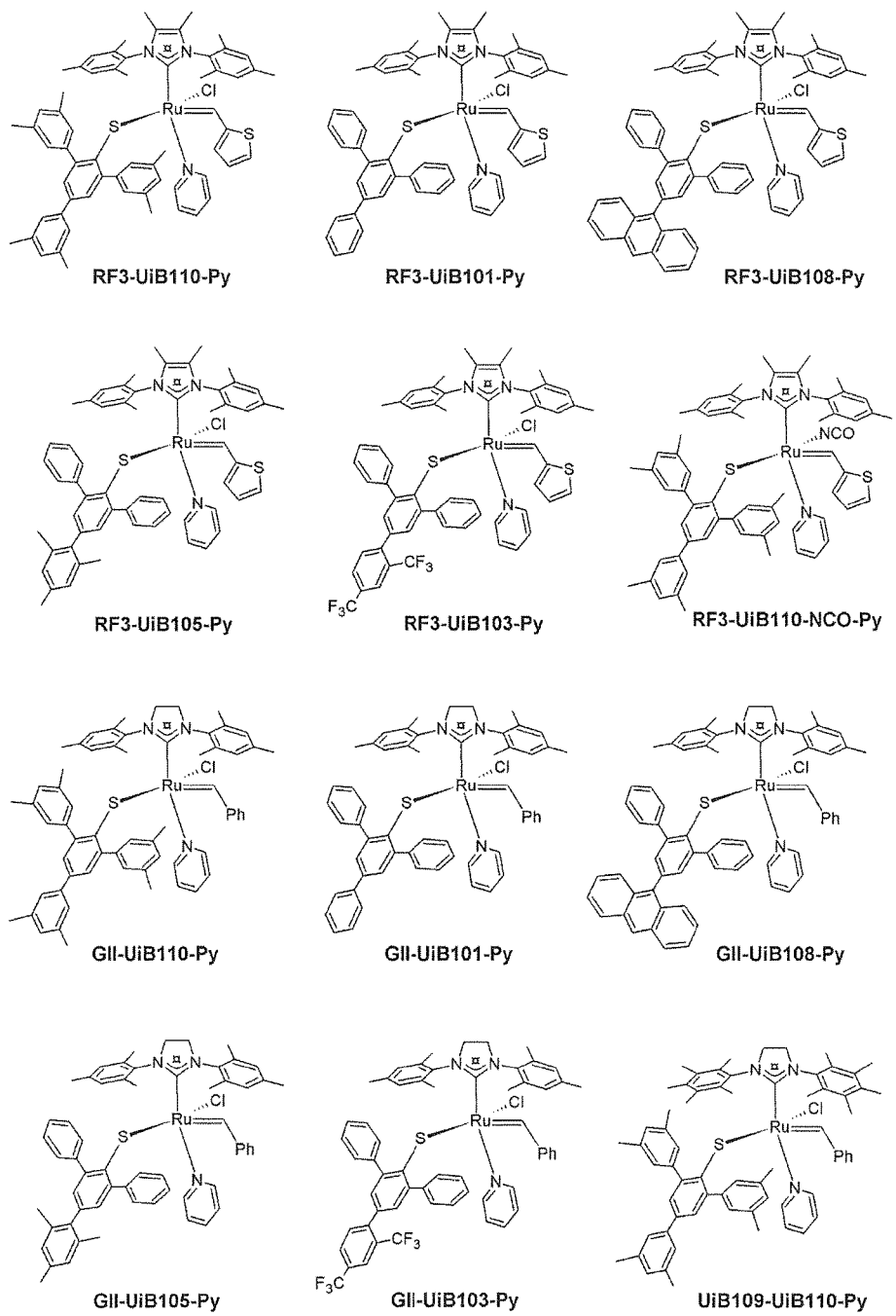
Figure 1:
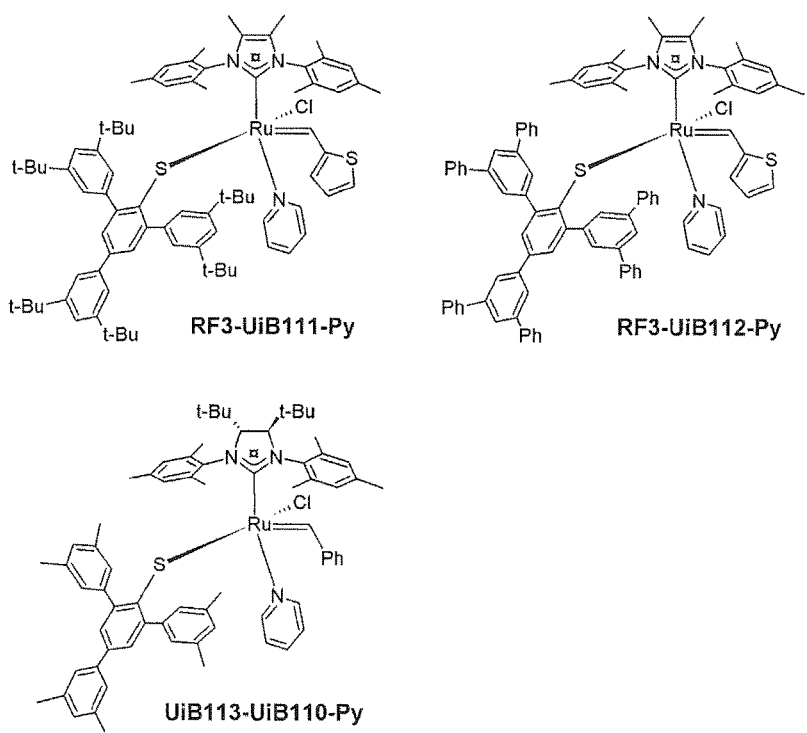

This application is a National Stage filing under 35 U.S.C. § 371 of International PCT Application No. PCT/EP2016/066286, filed Jul. 8, 2016, which claims priority to European Patent Application No. 15176276.2, filed Jul. 10, 2015, the entire contents of the aforementioned applications are hereby incorporated herein by reference.

The present invention refers to novel ruthenium complexes and their use as catalysts in olefin metathesis reactions, particularly to fast acting catalysts capable of predominantly giving the Z-isomers of olefinic products.

BACKGROUND OF THE INVENTION

Olefin metathesis is one of the most flexible ways to make carbon-carbon bonds in general and double bonds (C=C) in particular (1, 2, 3). The reaction formally cleaves two different carbon-carbon double bonds (C=C) into four fragments that are recombined into two new C=C double bonds to form olefinic products in which the original fragment partners are exchanged. The last years have seen an almost explosive increase in the use of this reaction for the production of fine chemicals, polymers and pharmaceuticals. The product of this transformation is in general a mixture of cis (Z) and trans (E) disubstituted isomers, with the thermodynamically more stable E-isomer usually being the major component. However, in certain instances the target product is either the pure E- or the pure Z-isomer.

For example, the biological, chemical and physical properties within a given pair of E- and Z-isomers may, in fact, be very different, highlighting the need for selective production of single isomers. The isomer mixtures produced have to be subjected to costly separation processes. Sometimes, the separation may be very challenging (4).

Catalysts for olefin metathesis have evolved rapidly in the past few decades. The catalyst is the main key to controlling the ratio with which the isomers are formed and the availability of robust and industrially compatible stereoselective catalysts is expected to expand the applicability of olefin metathesis in organic synthesis and polymerisation chemistry (3). Such catalysts would have a particular impact on the synthesis of large macrocycles by ring closing metathesis (RCM), strereoregular polymers (ROMP), and stereisomeric pure alkenes. The Z-alkene functionality is, in fact, required in many cases, either because it is present in the target molecule or because it is necessary for subsequent stereospecific transformations. A range of natural products with biological activity (e.g. anticancer, antibacterial, and antifungal) contain Z-alkene macrocyclic frameworks, see Table 1. In most of the cases, the cost of extraction of these molecules is prohibitive, and total synthesis is the only alternative (4, 5). The formation of such large rings is very challenging, with RCM standing out among the few alternative routes (1, 5, 6).

The stereochemical outcome depends on many factors such as the nature of the substrate and of the catalyst, the reaction conditions and on the presence of specific additives (7-10). Time consuming and very costly empirical approaches are therefore required to improve the process of manufacturing the individual molecules. Hence, the quest for efficient stereoselective catalysts is to a large extent driven by commercial needs (3).

In recent years, several highly Z-selective catalysts have been discovered. The first examples were disclosed by Schrock and Hoveyda (11-14). These catalysts are based on molybdenum or tungsten and are capable of promoting metathesis transformations such as ring opening/cross metathesis (ROCM) (12), ring opening metathesis polymerisation (ROMP) (13), olefin homocoupling (14), cross-metathesis (CM) (15, 16), and RCM (17, 18).

More recently highly Z-selective ruthenium-based catalysts have been discovered. Grubbs and co-workers have developed Ru-catalysts involving a bidentate N-heterocyclic carbene (NHC)-adamantyl ligand. These catalysts have shown high selectivity in several processes: cross-metathesis (CM) (19), olefin homocoupling (20, 21), ring opening metathesis polymerisation (ROMP) (22, 23), ring closing metathesis (RCM) (24, 25), and ring opening/cross-metathesis (ROCM) (26). A different system, containing one 2,4,6-triphenylbenzenethiolate ligand has so far demonstrated high Z-selectivity in homocoupling reactions (27, 28). Hoveyda and coworkers have developed another highly Z-selective system containing a dithiolate ligand (29), which has been applied in ring opening metathesis polymerisation (ROMP) and ring-opening/cross-metathesis (ROCM).

U.S. Pat. Nos. 5,312,940, 5,342,909, 5,969,170, 6,111,121, 6,635,768 and 6,613,910, international patent applications WO 98/21214, WO 00/71554 and WO 2004/112951 disclose pentacoordinated ruthenium and osmium olefin metathesis catalysts. The content of those documents is herein incorporated by reference. These catalysts have the general structure:

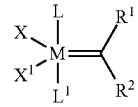

wherein M is the metal, L and $L^1$ are neutral ligands, $R^1$ and $R^2$ are H or organic moieties and X and $X^1$ are anionic ligands.

Similarly, hexacoordinated ruthenium and osmium olefin metathesis catalysts have also been disclosed, in U.S. Pat. No. 6,818,586 and US patent application US 2003/0069374. The content of those documents is herein incorporated by reference. These catalysts have the general structure:

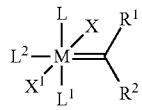

wherein M is the metal, L, $L^1$ and $L^2$ are neutral ligands, $R^1$ and $R^2$ are H or organic moieties and X and $X^1$ are anionic ligands.

In both the pentacoordinated and the hexacoordinated catalysts the two anionic ligands X and $X^1$ are preferably selected from halide and carboxylate anions. None of these catalysts, however, exhibit significant Z-stereoselectivity.

U.S. Pat. No. 7,094,898 and US patent application US 2005/0131233 disclose ruthenium-based olefin metathesis catalysts with a high rate of catalytic turnover and a high degree of stability. The content of those documents is herein incorporated by reference. The catalysts described in these documents have anionic ligands with the structure Z-Q, wherein each Z may comprise O, S, N or C and each Q comprises a planar electron-withdrawing group.

These documents also describe three novel asymmetrically substituted complexes Ru(OC$_6$Cl$_5$)Cl(CHPh)(IMes)(py), Ru(OC$_6$Br$_5$)Cl(CHPh)(IMes)(py) and (Ru(OC$_6$Br$_5$)Cl(CHPh)(IMes)(3-Br-py) that display a weak Z-stereoselectivity in the RCM of 5-hexen-1-yl 10-undecenoate to give oxa-cyclohexadec-11-en-3-one (Exaltolide). The product obtained using these catalysts contains 9-12% more of the Z-isomer than when using a symmetrically substituted catalyst. However, the Z-stereoselectivity of these asymmetrically substituted catalysts turns out not to be general. For example, in another RCM reaction reported in the same patent, the percentage of the Z-isomer product obtained using the asymmetrically substituted catalysts Ru(OC$_6$Cl$_5$)Cl(CHPh)(IMes)(py) and Ru(OC$_6$Br$_5$)Cl(CHPh)(IMes)(py)) is very similar to that obtained using two symmetrically substituted catalysts, RuCl$_2$(CHPh)(IMes)(py$_2$) and Ru(OC$_6$F$_5$)$_2$(CHPh)(IMes)(py).

These documents also report a ruthenium olefin metathesis catalyst with an anionic ligand in which a sulphur atom is bound to ruthenium (Ru(SC$_6$F$_5$)$_2$(CHPh)(IMes)(py)). However, only partial characterisation, consisting of $^1$H-NMR and $^{19}$F NMR spectra, is provided for this compound. This catalyst displays good catalytic activity, surpassing that of the corresponding oxygen-based catalyst Ru(OC$_6$F$_5$)$_2$(CHPh)(IMes)(py), for example in the RCM of the 1,9-decadiene to give cyclooctene. However, no particular E/Z stereoselectivity is reported for this catalyst.

WO 2012/032131 describes Z-stereoselective olefin metathesis catalysts based on ruthenium- and osmium metal complexes. The content of this document is herein incorporated by reference. In olefin metathesis reactions, the described catalysts selectively provide the thermodynamically less favoured Z-isomers.

EP 2 826 783 A1 describes ruthenium and osmium complexes for use as catalysts in olefin metathesis reactions. In addition to being Z-selective, the described catalysts provide superior stability in air and under protic conditions. In contrast to other Z-selective catalysts, they are able to effect Z-selective olefin metathesis in air, using non-degassed (i.e. stored under air) olefinic substrates and solvents.

However, there still remains a need for improved Z-selective catalysts with high catalytic activity and stability. In particular, there is a need for fast initiating catalysts that can promote olefin metathesis transformations within a broad range of temperatures. Further, there is a need for Z-selective catalysts with high olefin metathesis selectivity, i.e. low tendency to isomerization of the olefinic substrate.

The present invention addresses the above need for highly active and stereoselective olefin metathesis catalysts by providing a novel class of ruthenium-based catalysts.

SUMMARY OF THE INVENTION

The present invention relates to ruthenium complexes having a general formula (I) and isomers thereof:

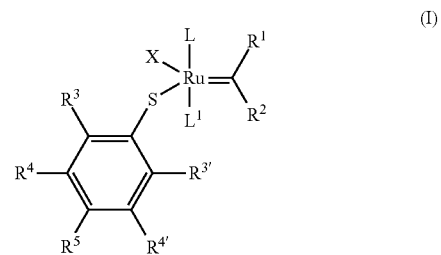

wherein
L is an N-heterocyclic carbene ligand,
L$^1$ is a monodentate ligand, comprising an aromatic N-heterocyclic compound, optionally substituted with one or more substituents, that is coordinated to Ru via a ring N-atom, or L$^1$ is absent,
X is halide or pseudohalide, e.g. —NCO, —CN, —CNO, —NCS, —N$_3$,
R$^1$ and R$^2$ are independently selected from the group consisting of H, C$_{1-20}$ alkyl, C$_{2-20}$ alkenyl, C$_{2-20}$ alkynyl, C$_{1-20}$ alkoxy, C$_{2-20}$ alkenyloxy, C$_{6-14}$ aryl, C$_{6-14}$ heteroaryl, C$_{6-14}$ aryloxy, C$_{6-14}$ heteroaryloxy, C$_{1-20}$ alkylcarboxylate, C$_{2-20}$ alkoxycarbonyl, C$_{1-20}$ alkylthio, C$_{1-20}$ alkylsufinyl and C$_{1-20}$ alkylsulfonyl, each optionally substituted with one or more substituents,
or R$^1$ and R$^2$ are covalently linked to form a 5- or 6-membered carbocyclic ring that may optionally be part of a bicyclic molecule and which may optionally be substituted with one or more substituents,
R$^3$, R$^{3'}$, R$^4$, R$^{4'}$ and R$^5$ are independently selected from the group consisting of H, C$_{1-20}$ alkyl, C$_{2-20}$ alkenyl, C$_{2-20}$ alkynyl, C$_{1-20}$ alkoxy, C$_{2-20}$ alkenyloxy, C$_{6-14}$ aryl, C$_{6-14}$ heteroaryl, C$_{6-14}$ aryloxy, C$_{6-14}$ heteroaryloxy, C$_{1-20}$ alkylcarboxylate, C$_{2-20}$ alkoxycarbonyl, C$_{1-20}$ alkylthio, C$_{1-20}$ alkylsulfinyl and C$_{1-20}$ alkylsulfonyl, each optionally substituted with one or more substituents, and
no more than three of R$^3$, R$^{3'}$, R$^4$, R$^{4'}$ and R$^5$ are H.

The inventors found that ruthenium complexes of the above formula (I) are particularly suitable for use as catalysts in olefin metathesis reactions and provide a surprisingly high activity. The new catalysts are able to promote a Z-selective olefin metathesis reaction much faster than the previous ones. Appreciable amounts of the product are typically formed within a few minutes at room temperature (e.g. 20-22° C.) instead of one or more hours and at higher temperature (e.g. 40-60° C.). Fast initiating catalysts for olefin metathesis known so far (43, 49 and 50) that provide a comparable reaction rate are not suitable to selectively generate the Z-product.

An additional advantage of the compounds of formula (I) is their high catalytic activity combined with their capability to generate higher yields of the olefin metathesis product. The formation of olefin metathesis product with ruthenium-based catalysts, under standard argon conditions and without additives, is generally accompanied by the isomerization of the starting material (33-36). In particular, with the previous catalysts disclosed in WO 2012/032131 the tendency to isomerize both starting materials and olefin metathesis products was particularly high (under standard argon conditions and without additives).(32, 28) In contrast, under similar standard conditions the new catalysts of formula (I) display a much lower tendency to isomerize both the starting material and the product. This allows achieving higher yield of the Z-product. This is particularly advantageous with those substrates which are easily isomerized in presence of ruthenium-based olefin metathesis catalysts (e.g. allylbenzene).(32,28)

Further, it was found that the new catalysts of formula (I) enable a broader range of application temperatures. The new catalysts can promote olefin metathesis transformations within a much broader range of temperatures (e.g. from 0 to above 100° C.). Indeed, a consequence of the fast initiation of the new catalysts is that olefin metathesis reaction is possible also at unusually low temperatures (e.g. at 0° C.). Moreover, despite the fact that a significant amount of the neutral donor ligand $L^1$ (e.g. pyridine) is dissociated in solution, the thermal stability of these complexes is excellent. For example, one of the new catalysts (5f) has been successfully tested at temperatures above 100° C. With the previous catalysts described in WO 2012/032131 it was found that the highest suitable temperature for catalytic reactions is about 60° C.

The new catalysts display also an improved functional group tolerance. In particular, these catalysts are able also to promote Z-selective metathesis of acidic substrates. For example, they are able to promote the metathesis homocoupling of terminal alkenoic acids (e.g. 10-Undecenoic acid and 4-pentenoic acid). These transformations were not possible with the previous catalysts.

Catalysts of the present invention surprisingly provide a high efficiency in promoting Ring Closing Metathesis (RCM) reaction in the synthesis of macrocycles. The new catalysts work particularly well, and display an excellent catalytic activity, at very high substrate dilution (e.g. 1-3 mM). High substrate dilution is generally required for achieving high yields in ring closing metathesis for the synthesis of medium- and large-sized rings. The new catalysts are efficient in promoting the formation of a 14-membered macrolactone, which is considered a relatively challenging target product, and high yields of the product could be achieved even at room temperature and at ambient pressure. In contrast, the previous catalysts possess negligible olefin metathesis activity under similar substrate dilution, and they are very poor catalysts in ring closing metathesis.

The inventors found that the above advantageous properties of the catalysts of the invention are mainly attributed to the at least bisubstituted thiolate ligand coordinated to ruthenium via the sulfur atom. When using other anionic ligands or even with unsubstituted thiolate, the same advantages could not be achieved.

In the compounds of Formula (I) L is a N-heterocyclic carbene (NHC) ligand, which may be optionally substituted. In terms of the invention, "N-heterocyclic carbenes" are heterocyclic compounds containing a divalent carbon atom (carbene carbon atom) bound to at least one nitrogen atom. The heterocycle may contain one or more additional heteroatoms preferably selected from N, O, S and combinations thereof, with the remaining ring atoms being carbon atoms. In a preferred embodiment, both ring atoms neighbouring the carbene carbon are nitrogen atoms. The size of the heterocyclic ring is preferably 5 or 6 ring atoms including the carbene carbon, most preferably 5 ring atoms. The heterocycle may optionally be part of a bicycle, e.g. benzimidazolylidene. According to a preferred aspect of the invention, L is selected from the group consisting of imidazol-2-ylidenes, dihydroimidazol-2-ylidenes, triazol-5-ylidenes, tetrazol-5-ylidenes, pyrazol-3-ylidenes, benzimidazol-2-ylidenes, oxazol-2-ylidenes, thiazol-2-ylidenes and cyclic alkyl amino carbenes, each optionally substituted.

"Cyclic alkyl amino carbenes" comprise a 5-membered ring, wherein one of the ring atoms neighboring the carbene carbon is a nitrogen atom and the other is a quaternary carbon, i.e. a ring carbon atom having two substituents, preferably two $C_{1-8}$ linear or branched alkyl substituents.

The N-heterocyclic carbenes L may optionally be substituted at one or more ring atoms. Substituents can be present at the ring atoms neighbouring the carbene carbon and/or at other ring atoms but not at the carbene carbon. Preferably, L is substituted at one or both ring atoms neighbouring the carbene C-atom and optionally at one or more additional ring atoms. For example, in case of L being imidazol-2-ylidene, it is preferably substituted at one or both N-atoms neighbouring the carbene carbon and/or at one or both ring C-atoms.

According to a preferred embodiment of the invention, substituents at one or more ring atoms of L are independently selected from $C_{1-6}$ alkyl groups and 5- or 6-membered aromatic or heteroaromatic rings, preferably phenyl, that may optionally be substituted with one or more substituents. Substituents at the 5- or 6-membered aromatic or heteroaromatic rings, particularly phenyl, are preferably selected from 1-5 linear or branched $C_{1-8}$ alkyl groups.

For ring N-atoms, substituents are preferably selected from 5- or 6-membered aromatic or heteroaromatic rings, preferably phenyl, that may optionally be substituted with one or more substituents, e.g. 1-5 linear or branched $C_{1-8}$ alkyl groups.

For ring C-atoms, substituents are preferably selected from $C_{1-6}$ alkyl groups, e.g. methyl or t-butyl.

Preferably, both ring atoms neighbouring the carbene C-atom of L, e.g. imidazol-2-ylidene, are substituted with phenyl groups that may in turn be substituted, preferably in o- and/or p-position, with one or more substituents, e.g. 1-5 linear or branched $C_{1-8}$ alkyl groups. It is particularly preferred, that both ring atoms neighbouring the carbene C-atom of L, e.g. imidazol-2-ylidene, are substituted with phenyl groups that are in turn substituted with 2-5 methyl groups.

Substituents at ring positions of L, e.g. imidazol-2-ylidene, not neighbouring the carbene C-atom are preferably selected from linear or branched $C_{1-6}$ alkyl groups, e.g. methyl or t-butyl.

In the compounds of Formula (I) $L^1$ is a monodentate ligand, comprising an aromatic N-heterocyclic compound, optionally substituted with one or more substituents, that is coordinated to Ru via a ring N-atom. According to the invention, $L^1$ is a rather weakly coordinating ligand. Exemplary aromatic N-heterocyclic compounds are pyrazole, imidazole, pyrazine, pyrimidine, pyridazine, and pyridine, each optionally substituted. Preferred substituents at $L^1$, e.g. pyridine, are independently selected from $C_{1-6}$ alkyl groups and 5- or 6-membered aromatic or heteroaromatic rings, preferably phenyl, that may optionally be substituted with one or more substituents. Substituents at the 5- or 6-membered aromatic or heteroaromatic rings, particularly phenyl, are preferably selected from 1-5 linear or branched $C_{1-8}$ alkyl groups.

Preferably, $L^1$ is pyridine, that may optionally be substituted with one or more substituents. It was found in the present invention, that pyridine is particularly advantageous in that it stabilizes the ruthenium complex and yet enables high catalytic activity over a broad range of reaction temperatures.

In an alternative embodiment of the invention, $L^1$ is absent. If the compounds of formula (I) are present in solid form, the substituent $L^1$ gives them stability, particularly towards air or humidity. However, in solution or in vacuum, the ligand $L^1$ may at least partially dissociate. Thus, the present invention also encompasses a mixture of compounds of formula (I), wherein in 0-100%, preferably 1-80%, 10-60% or 20-40%, of the compounds of formula (I), the ligand $L^1$ is absent. In the remaining compounds of formula (I), $L^1$ preferably is pyridine, which may optionally be substituted. According to a preferred aspect of this embodiment of the invention, a mixture of compounds of formula (I), wherein $L^1$ is pyridine, and compounds of formula (I), wherein $L^1$ is absent, is present in a solution in an organic solvent, such as benzene, toluene, xylene and p-cymene.

X is selected from halides, (i.e. F, Cl, Br and I), and pseudohalides (e.g. —NCO, —CN, —CNO, —NCS, or —$N_3$). Preferably, X is Cl or —NCO.

The groups $R^1$ and $R^2$ can be independently selected from the group consisting of H, $C_{1-20}$ alkyl, $C_{2-20}$ alkenyl, $C_{2-20}$ alkynyl, $C_{1-20}$ alkoxy, $C_{2-20}$ alkenyloxy, $C_{6-14}$ aryl, $C_{6-14}$ heteroaryl, $C_{6-14}$ aryloxy, $C_{6-14}$ heteroaryloxy, $C_{1-20}$ alkylcarboxylate, $C_{2-20}$ alkoxycarbonyl, $C_{1-20}$ alkylthio, $C_{1-20}$ alkylsufinyl and $C_{1-20}$ alkylsulfonyl, each optionally substituted with one or more substituents.

Suitable substituents at $R^1$ and/or $R^2$ are for example $C_{1-5}$ (halo) alkyl, halo, $C_{1-5}$ (halo) alkoxy, or phenyl optionally substituted with halo, $C_{1-5}$ (halo) alkyl or $C_{1-5}$ (halo) alkoxy.

According to a preferred embodiment, one of $R^1$ and $R^2$ is H and the other is a 5- or 6-membered aromatic or heteroaromatic ring, preferably selected from the group consisting of phenyl, thiophenyl, furanyl, pyridinyl, imidazolinyl, pyranyl, thiopyranyl, pyrrolyl, pyrazolyl, oxazolyl, isoxazolyl, thiazol and isothiazol, that may optionally be substituted with one or more substituents. For example, one of $R^1$ and $R^2$ is H and the other is phenyl or thiophen-2-yl.

According to an alternative embodiment, $R^1$ and $R^2$ are covalently linked to form a 5- or 6-membered carbocyclic ring that may optionally be part of a bicyclic molecule and which may optionally be substituted with one or more substituents. Suitable substituents at $R^1$ and/or $R^2$ are for example $C_{1-5}$ (halo) alkyl, halo, $C_{1-5}$ (halo) alkoxy, or phenyl optionally substituted with halo, $C_{1-5}$ (halo) alkyl or $C_{1-5}$ (halo) alkoxy.

According to a preferred embodiment, $R^1$ and $R^2$ together with the carbon atom to which they are attached form an indenylidene ligand (more particularly a 1H-indene-1-ylidene group), which may optionally be substituted at one or more ring positions. For example, a 1H-indene-1-ylidene group may be substituted with a phenyl group, preferably in the 3' position.

In the compounds of formula (I), no more than three of $R^3$, $R^{3'}$, $R^4$, $R^{4'}$ and $R^5$ are H. This means, the thiophenyl moiety is at least bisubstituted. For example, $R^4$, $R^{4'}$ and $R^5$ are H and $R^3$ and $R^{3'}$ (the residues at the ortho positions) are as defined above.

Substituents at $R^3$, $R^{3'}$, $R^4$, $R^{4'}$ and $R^5$ may independently be selected from the group consisting of $C_{1-6}$ alkyl, phenyl and $CF_3$.

Preferably, $R^3$ and $R^{3'}$ are phenyl, optionally substituted with one or more substituents, preferably in meta and/or para positions but not in ortho positions.

$R^4$ and $R^{4'}$ are preferably H.

$R^5$ is preferably H, phenyl or anthracenyl, optionally substituted with one or more substituents.

The compounds of general formula (I) can be provided in solid form or in solution in an organic solvent. Suitable solvents include benzene, toluene, xylene and p-cymene. In solution, the ligand $L_1$ may at least partially dissociate from the compounds of formula (I). Accordingly, a solution of compounds of formula (I) may comprise a mixture of compounds of formula (I), wherein in 0-100%, preferably 1-80%, 10-60% or 20-40%, of the compounds of formula (I), the ligand $L_1$ is absent. In the remaining compounds of formula (I), $L_1$ is an aromatic N-heterocyclic compound as defined herein above, preferably pyridine, which may be substituted or unsubstituted. When provided in solid form, the compounds of formula (I) preferably have a ligand $L_1$. When dissolved, $L_1$ may at least partially dissociate from the ruthenium complex.

The compounds of the present invention are suitable as catalysts, e.g. for catalysing olefin metathesis reactions. Thus, a further aspect of the present invention is a catalyst for catalysing olefin metathesis reactions comprising a compound for formula (I) as described above. Preferably, the catalyst is capable of stereoselectively generating Z-isomeric products in olefin metathesis reactions. The olefin metathesis reaction may comprise a reaction selected from ring-closing metathesis, ring-opening metathesis, metathesis homocoupling, cross-metathesis, ring opening metathesis polymerization, and ring opening/cross metathesis. Preferred reactions are metathesis homocoupling, cross-metathesis, and ring-closing metathesis.

In preferred aspects, the catalysts are capable of stereoselectively and/or regioselectively generating Z-isomeric products. In especially preferred aspects, the catalysts are capable of stereoselectively generating Z-isomeric products in ring-closing metathesis reactions. In representative catalysed olefin metathesis reactions the Z/E selectivity using the novel catalysts is at least 10%, at least 20% or at least 30% (calculated on the total yield of Z and E products) higher than that obtained using (1,3-Bis-(2,4,6-trimethylphenyl)-2-imidazolidinylidene)dichloro(o-isopropoxyphenylmethylene)ruthenium. Further, in representative catalyzed olefin metathesis reactions, the inherent Z-selectivity (i.e. the Z-selectivity at low substrate conversion) of the catalysts of the invention is similar to that of (2,4,6-triphenylbenzenethiolate)-(Cl)-(1,3-dimesityl-4,5-dihydroimidazol-2-ylidene)-(2-isopropoxybenzylidene)-ruthenium. However, the yield of the Z-product, which is achieved with the new catalysts of the invention, is in general much higher than that obtained with previous catalysts (e.g. (2,4,6-triphenylbenzenethiolate)-(Cl)-(1,3-dimesityl-4,5-dihydroimidazol-2-ylidene)-(2-isopropoxybenzylidene)-ruthenium.

In other aspects, the invention provides for a method of catalysing an olefin metathesis reaction comprising introducing any compound presented herein in a reaction medium comprising an olefin.

In other aspects, the method of catalysing an olefin metathesis reaction comprises introducing a compound of formula (I) into a reaction medium comprising an olefin.

The reaction conditions of the olefin metathesis reaction may vary over a broad range. The temperature can e.g. be from 0-100° C. or above. As a consequence of the fast initiation of the new catalysts, olefin metathesis is possible even at low temperatures, e.g. at a temperature of 0-30° C., 1-20° C. or 5-10° C. Further, due to the high thermal stability of the complexes of formula (I), the metathesis reaction can be performed even at high temperatures, e.g. at 60-100° C. or even above 100° C., for example 80-100° C. It was further found that the catalysts of formula (I) work particularly well and display an excellent catalytic activity at high substrate dilution (e.g. 1-3 mM). Thus, a preferred embodiment of the invention is a method of catalyzing an olefin metathesis reaction at high substrate dilution of 1-3 mM.

High substrate dilution is generally required to achieve high yields in ring-closing metathesis with a synthesis of medium- and large-sized rings.

In other aspects, the olefin metathesis reaction comprises reactions selected from ring-closing metathesis, ring-opening metathesis, metathesis homocoupling, cross-metathesis, ring opening metathesis polymerization, or ring opening/cross metathesis.

In other aspects, the method stereoselectively and/or regioselectively generates disubstituted olefin products in a ring-closing metathesis, ring-opening metathesis, metathesis homocoupling, cross-metathesis, ring opening metathesis polymerization reaction, or ring opening/cross metathesis.

In another aspect, the method results in products where the Z/E selectivity is at least 10% (calculated on the total yield of Z and E products) higher than that obtained using (2,4,6-triphenylbenzenethiolate)-(Cl)-(1,3-dimesityl-4,5-dihydroimidazol-2-ylidene)-(2-isopropoxybenzylidene)-ruthenium. In another aspect, the method of the invention achieves a Z/E-selectivity comparable to that obtained using (2,4,6-triphenylbenzenethiolate)-(Cl)-(1,3-dimesityl-4,5-dihydroimidazol-2-ylidene)-(2-isopropoxybenzylidene)-ruthenium. However, the yield of the Z-product, which can be achieved in a method of the invention using the new catalysts of formula (I), is in general much higher than that obtained with previous catalysts (e.g. (2,4,6-triphenylbenzenethiolate)-(Cl)-(1,3-dimesityl-4,5-dihydroimidazol-2-ylidene)-(2-isopropoxybenzylidene)-ruthenium).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

The catalyst of the present invention may be free in the reaction medium or bound to a solid support, e.g. inorganic supports such as glass beads, silica, zeolite, alumo silicates or magnetic beads, or organic supports such as sepharose or polystyrene.

Compounds according to the present invention were characterised and/or provided by density functional theory calculations as well as by experimental reactions.

Definitions

In order that the invention may be more readily understood, certain terms are first defined here for convenience.

The terms "isolated", "purified", or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The terms "a", "an", and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about", when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Furthermore the compounds of the invention include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a $C_{1-6}$ alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "haloalkoxy" refers to an —O-alkyl radical that is substituted by one or more halo substituents. Examples of haloalkoxy groups include trifluoromethoxy, and 2,2,2-trifluoroethoxy.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" or "heterocyclyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, mercaptoalkoxy, N-hydroxyamidinyl, or N'-aryl, N"-hydroxyamidinyl.

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2$^{nd}$ Edition*, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more.

The term "salts" is meant to include salts of the compounds which are prepared with acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention is further illustrated by the following figures and examples.

FIGURES

FIG. 1 shows exemplary compounds of formula (I).

Figure 2:
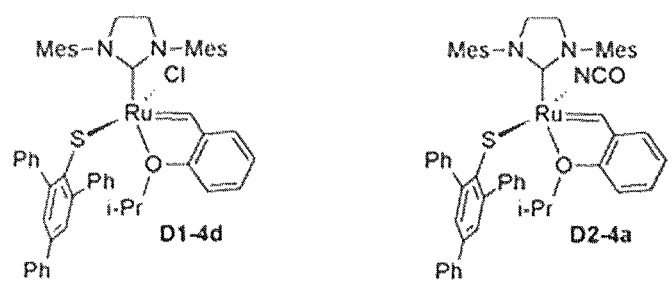

FIG. 2 shows the Lewis structure of comparative catalysts D1-4d described in references 27, 28 and 47 and D2-4a described in references 32 and 48.

EXPERIMENTAL

All reactions were performed under dry argon atmosphere, either inside a glovebox or using Schlenk techniques, unless otherwise stated. Tetrahydrofuran, toluene, and hexane, were purified using an MBraun solvent purification system ("Grubbs' column"). Tetrahydrofuran was dried overnight over KH and filtered through celite before use. Anhydrous pentane was purchased from Sigma-Aldrich and used as received. Pyridine was purchased from Sigma-Aldrich and degassed before use.

$CDCl_3$ was dried over $CaH_2$ and distilled before use, while anhydrous $C_6D_6$ was purchased from Sigma-Aldrich and degassed before use. Allylacetate, allyl boronic acid pinacol ester, allylbenzene, 1-octene, 4-phenyl-1-butene, N-allylaniline, 2-(allyloxy)-ethanol, 10-undecenoic acid, and 4-pentenoic acid were purchased from Sigma-Aldrich and degassed before use. Allylbenzene and 2-(allyloxy)-ethanol were additionally dried over molecular sieves 4 Å and passed through a column of activated basic alumina respectively before use. The aryl thiols, 2,4,6-Triphenylbenzenethiol (1a) 2,6-diphenyl-4-(9-anthracenyl)benzenethiol (1e), 2,4,6-tris(3,5-dimethylphenyl)benzenethiol (1f), and 2,4,6-tris(3,5-ditertbutylphenyl)benzenethiol (1g) were purchased from Santai Labs and used as received. The ruthenium catalyst catMETium® RF3 (3) was kindly supplied by Evonik Industries. Basic alumina (Sigma-Aldrich) was heated was heated for 60 hours at 220° C. under vacuum before use. All the other chemicals were purchased from Sigma-Aldrich and used as received.

The ruthenium catalysts 6 (43), 8 (44), and 12 (45), and the dienes 22 (24) and 24 (24) used for testing ring closing metathesis were prepared according to literature procedure.

Potassium 2,4,6-Triphenylbenzenethiolate 2a was prepared according to literature procedure (32), while the potassium thiolates 2e, 2f, and 2g were prepared using the following procedure: In a glovebox, KH (1.43 mmol) was added in small portions to a stirred solution of the corresponding thiol (i.e. 2,6-diphenyl-4-(9-anthracenyl)benzenethiol (1e), 2,4,6-tris(3,5-dimethylphenyl)benzenethiol (1f), and 2,4,6-tris(3,5-ditertbutylphenyl)benzenethiolate (1g) (1.36 mmol)) in THF (5 mL). The mixture was stirred at room temperature for 24 hours, the solvent removed under reduced pressure and the residue was washed three times with pentane, isolated over a frit and dried in the glove box. The quality of the product was evaluated by $^1$H-NMR spectroscopy, which showed the disappearance of the thiol proton peak at 3.64 (2e), 3.55 (2f), and 3.59 (2g) ppm ($CDCl_3$) respectively. The ruthenium complex 4 was prepared according the procedure described below.

Preparation of Ruthenium Complex 4

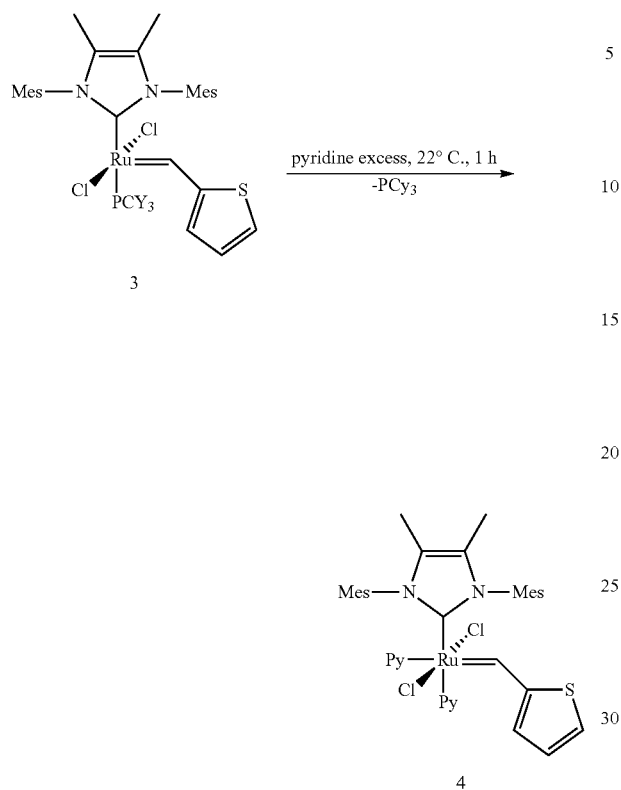

In a glovebox, a 25 mL vial, equipped with a magnetic stirring bar and a screw cap, was charged with complex 3 (1087 mg, 1.234 mmol) and pyridine (4 mt). The vial was closed and the mixture stirred at room temperature for 1 hour. Then pentane (5 mL) was added to the reaction mixture causing the precipitation of a green solid. The solid was allowed to sediment (settle out) and then was isolated by vacuum filtration through a frit, washed three times with 5 mL of pentane and dried in the glovebox to give 786 mg (84% of yield). 1H NMR (600.17 MHz, $C_6D_6$): δ=19.10 (s, 1H), 9.15 (s, 2H), 8.69 (s, 2H), 7.76 (br s, 1H), 7.42 (d, J=4.8, 1 H), 6.83 (br t, J=6.7, 1 H), 6.76-6.44 (br m, 7 H), 6.38 (br t, J=6.7, 1 H), 6.18-6.03 (br m, 2H), 2.50 (br s, 12H), 2.07 (br s, 6 H), 1.51 (s, 6 H). $^{13}C\{^1H\}$ NMR (150.91 MHz, $C_6D_6$): δ=289.11, 182.49, 164.83, 152.62, 150.88, 138.38, 135.83, 135.21, 134.29, 132.81, 130.08, 129.38, 128.35, 127.18, 122.92, 122.62, 21.16, 19.85 (br), 9.46.

NMR spectra were recorded on Bruker Biospin AV 500, AV 600, and AV III HD 850 spectrometers. The chemical shifts are reported relative to the residual solvent peaks. (46) Elemental analyses were performed using an Elementar Vario EL III analyzer. The DART mass spectrum was recorded by means of a DART-100 ion source from Ion-Sense Inc. (Saugus, Mass., USA) interfaced to an AccuTOF™ atmospheric ionization mass spectrometer from JEOL USA, Inc. (Peabody, Mass., USA). The AccuTOF™ mass spectrometer was operated with an orthogonal electrospray ionization source (ESI), an orthogonal accelerated time of flight (TOF) single stage reflectron mass analyzer and a dual micro channel plate (MCP) detector.

EXAMPLE 1

Preparation of Ruthenium Complex 5e

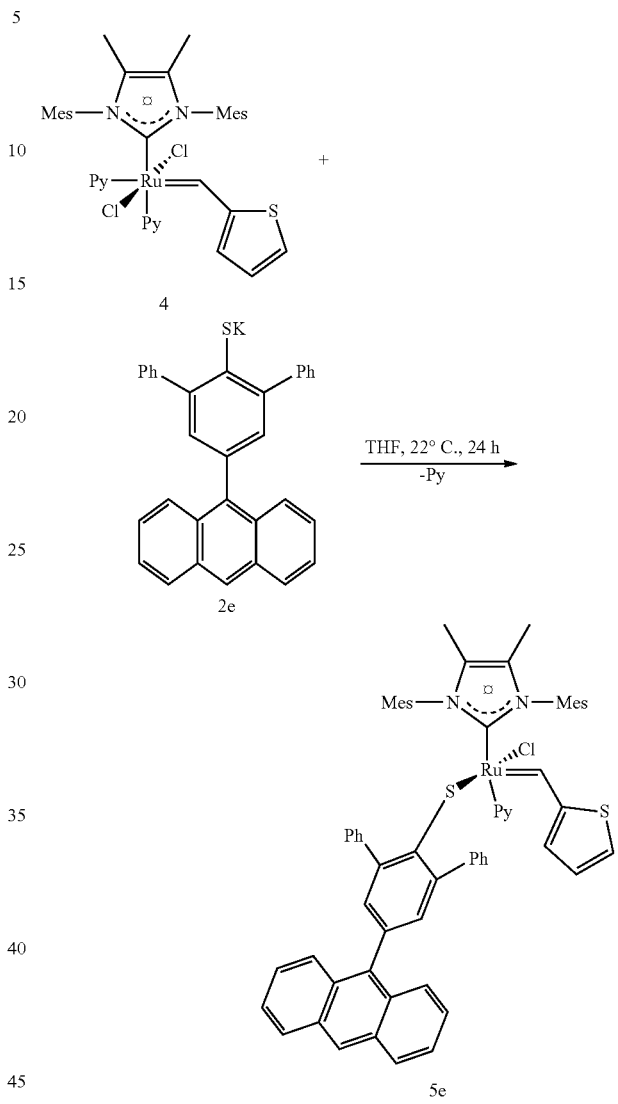

In a glovebox, a 25 mL vial, equipped with a magnetic stirring bar and a screw cap, was charged with complex 4 (100 mg, 0.132 mmol), potassium 2,6-diphenyl-4-(9-anthracenyl)benzenethiolate (68 mg, 0.143 mmol) 2e and tetrahydrofuran (5 mL). After the addition of the solvent the color of the suspension changed rapidly from green to brown. The mixture was stirred at room temperature for 18 hours, and then filtered through a short pad of celite. The solvent was reduced to about 2 mL under reduced pressure and then 20 mL of pentane were slowly added to the filtrate and the mixture was placed in the freezer (−32° C.) for a couple of days. The yellow-brown solid was isolated and further purified by repeating three times the following procedure: the solid was dissolved in about 2 mL of tetrahydrofuran followed by a slowly addition of about 20 mL of pentane. The mixture was placed in the freezer (−32° C.) for a couple of days, and the yellow-brown solid was isolated and washed three times with pentane. After the above described procedure the solid was dried in the glove box to give 62 mg (43%) of the title compound 5e. $^1H$ NMR (600.17 MHz, C$_6$D$_6$): δ=17.26 (br s, 0.98 H), 17.09 (br s, 0.02 H), 8.67-5.75 (br m, 24 H), 8.17 (s, 1 H), 7.81 (d, J=8.9, 4H), 6.75 (t, J=7.5, 2 H), 6.30 (t, J=6.3, 2 H), 3.31-1.48 (br m, 18 H), 1.40 (s, 6 H). $^{13}$C{$^1$H} NMR (150.91 MHz, C$_6$D$_6$): δ=260.92 (br m), 179.01 (br), 154.72, 149.98 (br), 149.12 (br), 144.54 (br), 142.76, 138.20 (br), 137.87, 137.41, 135.12, 134.39, 134.06, 132.80, 131.89, 130.45 (br), 130.02, 129.69, 127.59, 126.63, 125.94, 125.14, 122.70, 21.45, 19.95 (br), 9.16. Elemental analysis, calculated for C$_{65}$H$_{58}$ClN$_3$RuS$_2$: C, 72.16; H, 5.40; N, 3.88; found: C, 72.51; H, 5.39; N, 3.82.

EXAMPLE 2

Preparation of Ruthenium Complex 5f

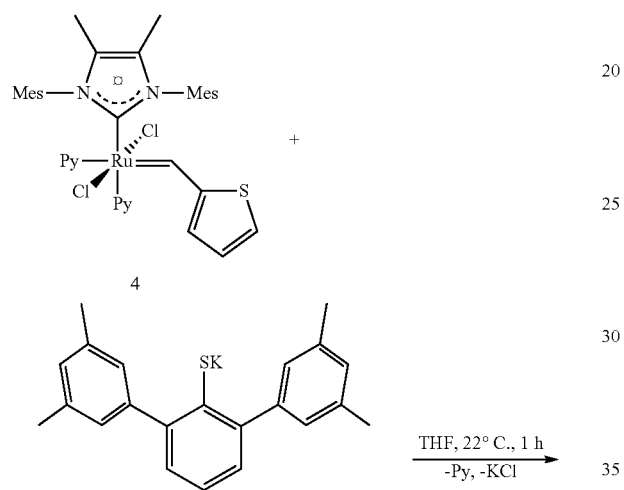

In a glovebox, a 25 mL vial, equipped with a magnetic stirring bar and a screw cap, was charged with complex 4 (100 mg, 0.132 mmol), potassium 2,4,6-tris(3,5-dimethyl-phenyl)benzenethiolate (65 mg, 0.141 mmol) 2f, and tetrahydrafuran (5 mL). After the addition of the solvent the color of the suspension changed rapidly from green to reddish-brown. The mixture was stirred at room temperature for 1 hour. The solvent was reduced to about 1 mL under reduced pressure. Then 10 mL of pentane were added and the resulting dark-brown mixture was rapidly filtered through a glass-fiber filter paper. The filtrate was placed in the freezer (−32° C.) for a couple of days. The red-brown solid was isolated, washed three times with pentane and dried in the glove box to give 99 mg (71%) of the title compound 5f. $^1$H NMR (600.17 MHz, C$_6$D$_6$): δ=17.71 (br s, 0.47 H), 17.15 (br s, 0.53 H), 8.53 (br d, J=4.0, 1.04 H), 8.02-7.78 (br m, 1.35 H), 7.54 (d, J=4.8, 0.46 H), 7.46-7.25 (m, 2.60 H), 7.07-6.44 (m, 11.42 H), 6.33-5.98 (br m, 1.53 H), 2.81 (s, 1.32 H), 2.52-2.32 (br m, 16.34 H), 2.25 (br s, 1.59 H), 2.17 (br s, 2.62 H), 2.09 (s, 6.89 H), 2.03 (s, 2.94 H), 1.58 (br s, 2.20), 1.50 (br s, 1.40 H), 1.40 (br s, 1.52 H), 1.32 (s, 3.50 H). $^{13}$C{$^1$H} NMR (150.91 MHz, C$_6$D$_6$): δ=260.62, 184.84, 175.19, 165.09, 153.92, 152.01, 145.52, 143.76, 141.40, 141.27, 139.40, 138.83, 138.63, 138.35, 138.07, 138.01, 137.70, 137.04 (br), 136.83, 136.39, 136.17 (br) 135.80, 135.17, 134.12 (br), 134.05, 133.96, 133.63 (br), 129.93 (br), 129.64, 129.29, 129.17 (br), 129.11 (br), 128.94 (br), 128.67, 128.35, 124.98, 124.73, 123.48, 122.38, 30.49, 30.22, 22.02 (br), 21.78 (br), 21.56, 21.51, 21.42, 21.35, 21.10, 20.41, 19.98, 19.64, 19.77, 17.88, 9.17, 9.02, 8.94. Elemental analysis, calculated for C$_{63}$H$_{66}$ClN$_3$RuS$_2$: C, 70.99; H, 6.24; N, 3.94; found: C, 71.21; H, 5.91; N, 3.76. HRMS (DART): calculated for C$_{58}$H$_{62}$$^{35}$ClN$_2$$^{102}$RuS$_2$ [M−py+H]$^+$: m/z=987.30864, found: m/z=987.30990.

EXAMPLE 3

Preparation of Ruthenium Complex 5g

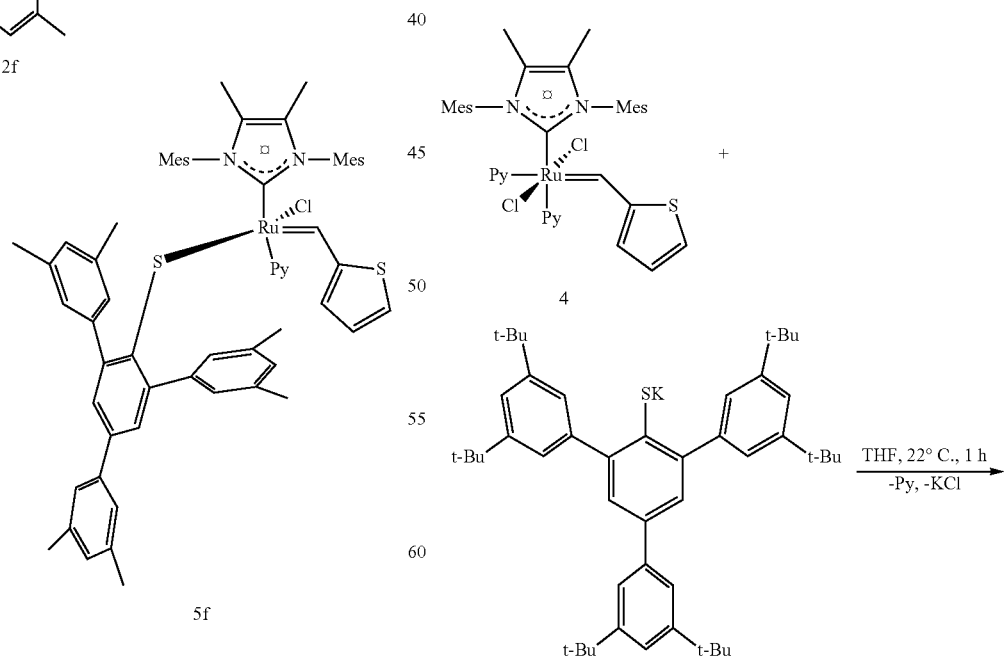

-continued

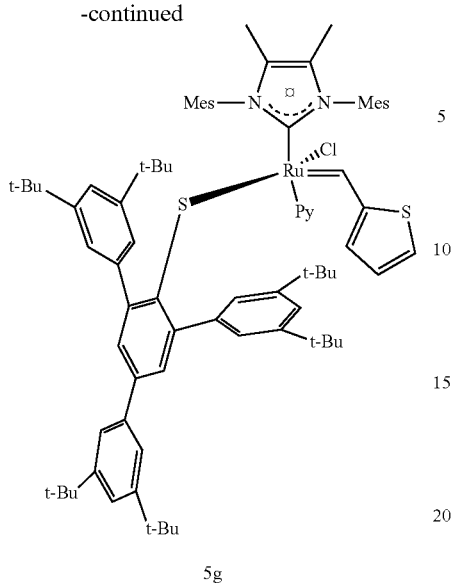

5g

In a glovebox, a 25 mL vial, equipped with a magnetic stirring bar and a screw cap, was charged with complex 4 (100 mg, 0.132 mmol) and potassium 2,4,6-tris(3,5-ditert-butylphenyl)benzenethiolate (105 mg, 0.147 mmol) 2g, and tetrahydrofuran (3 mL). After the addition of the solvent the color of the suspension changed rapidly from green to dark red-brown. The mixture was stirred at room temperature for 1 hour. The solvent removed under reduced pressure, the residue extracted with pentane and filtered through a glass-fiber filter paper. The dark brown filtrate was then placed in the freezer (−32° C.) for one week. The microcrystalline brown solid was isolated, washed with cold pentane, and dried in the glove box to give 95 mg (55%) of the title compound 5g. $^1$H NMR (600.17 MHz, $C_6D_6$): δ=18.95 (br s, 0.2 H), 17.35 (br s, 0.8 H), 8.54 (br m, 1.6 H), 8.34 (br s, 0.2 H), 8.14 (s, 1.6 H), 7.89 (s, 0.8 H), 8.05-7.94 (br m, 0.4 H), 7.69 (d, J=4.7, 0.8 H), 7.64-7.55 (br m, 2.6 H), 7.52 (s, 0.8 H), 7.49-7.37 (br m, 1.4 H), 7.31-7.26 (br m, 1.6 H), 7.10 (br m, 0.2 H), 7.03 (s, 1.6 H), 7.00-6.94 (br m, 0.8 H), 6.91 (s, 0.8 H), 6.86-6.77 (br m, 1.4 H), 0.6.76-6.47 (br m, 5.8 H), 6.37 (br t, J=6.2, 0.4 H), 6.26 (s, 0.4 H), 2.63-1.89 (br m, 18 H), 1.60-1.44 (br m, 27 H), 1.38-1.17 (br m, 27 H), 1.04-0.82 (br m, 6 H). Elemental analysis, calculated for $C_{81}H_{102}ClN_3RuS_2 \cdot C_5H_{12}$: C, 74.28; H, 8.26; N, 3.02; found: C, 74.05; H, 8.14; N, 3.03.

EXAMPLE 4

Dissociation of the Pyridine Ligand from Complexes 5e, 5f, and 5g in Benzene-$d_6$ Solution

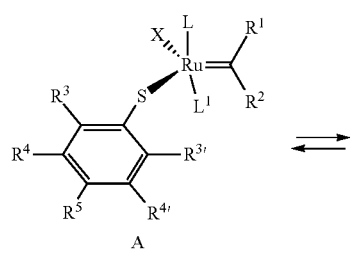

A

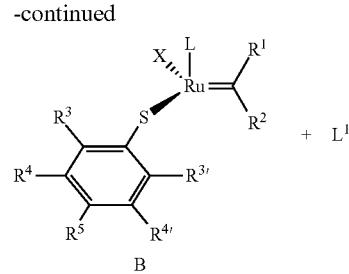

B

In a glove box, a NMR tube was charged with 0.5 mL of a benzene-$d_6$ solution of the 16-electron ruthenium complex (A), capped and wrapped with a layer of parafilm. The percentage of the 14-electron complex (B), which is formed upon the dissociation of the pyridine ligand ($L^1$) was determined by $^1$H-NMR at 293 K and 323 K.

| entry | complex | complex conc., (M) | % of B, 293 K | % of B, 323 K |
|---|---|---|---|---|
| 1 | 5e | 1 mM | 9 | 24 |
| 2 | 5f | 1 mM | 30 | 63 |
| 3 | 5f | 0.5 mM | 46 | 83 |
| 4 | 5f | 6 mM | 25 | 50 |
| 5 | 5g | 1 mM | 80 | 95 |

EXAMPLE 5

Preparation of Ruthenium Complex 5a

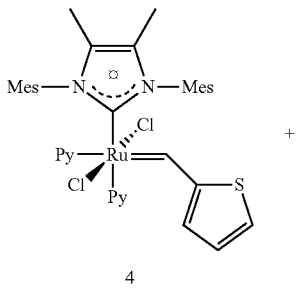

4

+

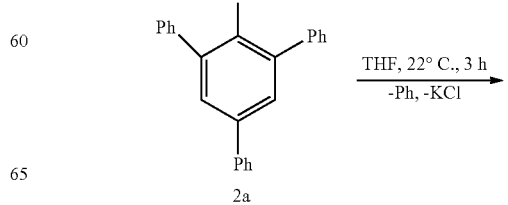

2a

-continued

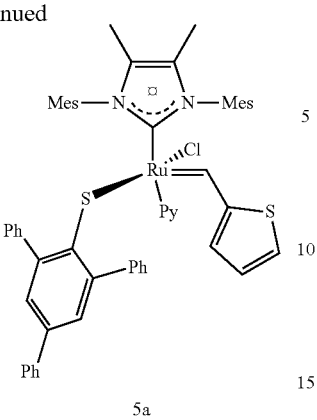

5a

In a glovebox, a 25 mL vial, equipped with a magnetic stirring bar and a screw cap, was charged with complex 4 (100 mg, 0.132 mmol), potassium 2,4,6-triphenylbenzenethiolate (56 mg, 0.155 mmol) 2a, and tetrahydrofuran (5 mL). After the addition of the solvent the color of the suspension changed rapidly from green to reddish-brown. The mixture was stirred at room temperature for three hours, during this time the color of the solution changes again from reddish-brown to dark-brown-greenish (the green color is due to the formation of a decomposition product). The solvent was removed under reduced pressure. The residual was extracted several times with pentane (in total about 20 mL) and the pentane solution was filtered through a short pad of celite. The solvent was again removed under vacuum and the dark-green residual was dissolved in 3 mL of toluene. Then 1 g of activated basic alumina and a stirring bar were added to the vial containing the toluene solution and the mixture was stirred for about 30 minutes. During this time the basic alumina becomes yellow-brownish and the toluene solution becomes dark green. The solution was removed with a Pasteur pipette and the impregnated basic alumina was washed repeatedly with 1 mL of toluene (7-8 times), until the color of the toluene extract was pale yellow. The resulting impregnated basic alumina, purified from the green colored decomposition product, was extracted two times with 100 μL of a solution of pyridine in toluene (10% vol) followed by 2 mL of toluene. The solvent was removed under vacuum, the residual dissolved in a minimum amount of toluene, and then 5 mL of pentane was slowly added until the solution became slightly cloudy. The vial was placer in the freezer (–32° C.) for a couple of days. The red-brown solid was isolated, washed three times with pentane and dried under vacuum to give 17 mg (12%) of 5a.$C_5H_{12}$. $^1$H NMR (600.17 MHz, $C_6D_6$, 283 K): δ=17.15 (br s, 0.97H), 16.90 (s, 0.03H), 9.17-8.92 (br, 1H), 7.88-7.22 (br m, 10H), 7.12-6.96 (m, 8H), 6.96-6.24 (br m, 8H), 6.24-5.06 (br, 2H), 2.88 (s, 0.09H), 2.80 (s, 2.91H), 2.45-2.26 (br m, 12H), 1.59 (s, 3H), 1.44 (s, 3H), 1.35 (s, 3H). $^{13}C\{^1H\}$ NMR (150.91 MHz, $C_6D_6$, 283 K): 276.34 (br), 272.39 (br), 179.41 (br), 164.87 (br), 157.77 (br), 153.32, 151.19, 150.08, 144.89, 144.50, 143.72, 141.12, 138.88, 138.38, 137.77, 137.48, 136.88 (br), 136.31, 136.19 (br), 135.08, 134.34, 133.84, 133.13 (br), 130.95, 130.65, 130.01, 129.23, 128.84, 128.35, 127.57, 127.48, 127.23, 126.77, 126.62, 125.94, 125.73, 122.24, 21.46, 21.31, 21.14, 20.55, 19.95, 19.63, 19.21, 17.96, 9.69, 9.20, 9.02. Elemental analysis, calculated for $C_{57}H_{54}ClN_3RuS_2$: C, 69.74; H, 5.54; N, 4.28; found: C, 69.51; H, 5.18; N, 3.99.

EXAMPLE 6

Preparation of Ruthenium Complex 7a

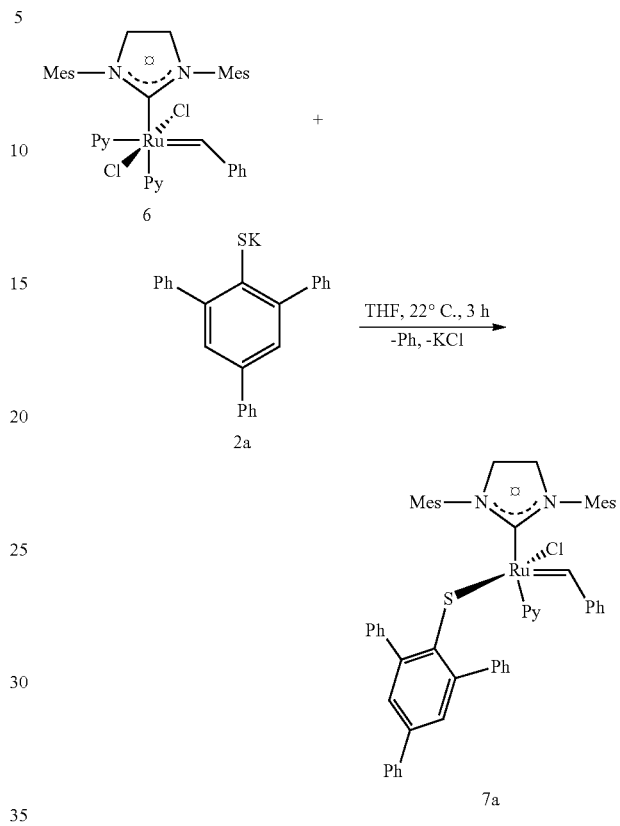

In a glovebox, a 25 mL vial, equipped with a magnetic stirring bar and a screw cap, was charged with complex 6 (100 mg, 0.138 mmol), potassium 2,4,6-triphenylbenzenethiolate (67 mg, 0.178 mmol) 2a, and tetrahydrofuran (5 mL). After the addition of the solvent the color of the suspension changed rapidly from green to reddish-brown. The mixture was stirred at room temperature for three hours, during this time the color of the solution changes from reddish-brown to dark-green (the green color is due to the formation of a decomposition product). The solvent was removed under reduced pressure. The residual was extracted several times with pentane (in total about 20 mL) and the pentane solution was filtered through a short pad of celite. The solvent was again removed under vacuum and the dark-green residual was dissolved in 3 mL of toluene. Then 1 g of activated basic alumina and a stirring bar were added to the vial containing the toluene solution and the mixture was stirred for about 30 minutes. During this time the basic alumina becomes yellow-green and the toluene solution becomes less intensely colored. The solution was removed with a Pasteur pipette and the basic alumina was washed repeatedly with 1 mL of toluene (7-8 times) until the color of the alumina was yellow-brown and the color of the toluene extract was pale yellow. The resulting impregnated alumina, was extracted two times with 100 μL of a solution of pyridine in toluene (10% vol) followed by 2 mL of toluene. The solvent was removed under vacuum, the residual dissolved in a minimum amount of toluene and pentane (about 5 mL) was slowly added until the solution became slightly cloudy. The vial was placed in the freezer (–32° C.) for a couple of days. The red-brown microcrystals were isolated, washed three times with pentane and dried under vacuum to give 38 mg (27%) of 7b.$C_5H_{12}$. $^1$H NMR (600.17 MHz, $C_6D_6$, 283 K): δ=17.90 (s, 0.98 H), 16.06 (s, 0.02 H), 9.75-8.04 (br, 1H), 8.07-7.28 (br, 9H), 7.28-7.03 (m, 5H), 7.03-6.98 (m, 4H), 6.98-6.73 (br, 6H), 6.72-6.45 (br, 2H), 6.45-6.30 (m, 2H), 6.26-5.33 (br, 1H), 3.14 (br m, 2H), 3.00 (br, 1H), 2.94 (br s, 3H), 2.62 (br s, 3H), 2.52 (br s, 3H), 2.35 (br s, 3H), 2.29 (br s, 3H), 1.65 (br s, 3H). $^{13}$C{$^1$H} NMR (150.91 MHz, $C_6D_6$, 283 K): 299.49, 214.20, 152.86 (br), 150.65, 150.25, 149.56, 144.94, 144.32, 142.96, 141.04, 139.36, 139.09, 137.47, 137.28, 136.85, 136.42, 136.20, 134.19, 131.54, 130.96, 130.42, 130.33, 129.93, 129.88, 129.45, 129.03, 128.83, 128.35, 127.98, 127.80, 127.54, 126.82, 126.73, 126.49, 125.99, 122.46, 51.73, 50.63, 24.34, 21.41, 21.27, 20.72, 19.61, 17.86. Elemental analysis, calculated for $C_{57}H_{54}ClN_3RuS$: C, 72.09; H, 5.73; N, 4.42; found: C, 72.45; H, 5.85; N, 4.15. HRMS (DART): calculated for $C_{52}H_{50}{}^{35}ClN_2{}^{102}RuS$ [M−py+H]$^+$: m/z=871.2427, found: m/z=871.2440.

EXAMPLE 7

Preparation of Ruthenium Complex 7f

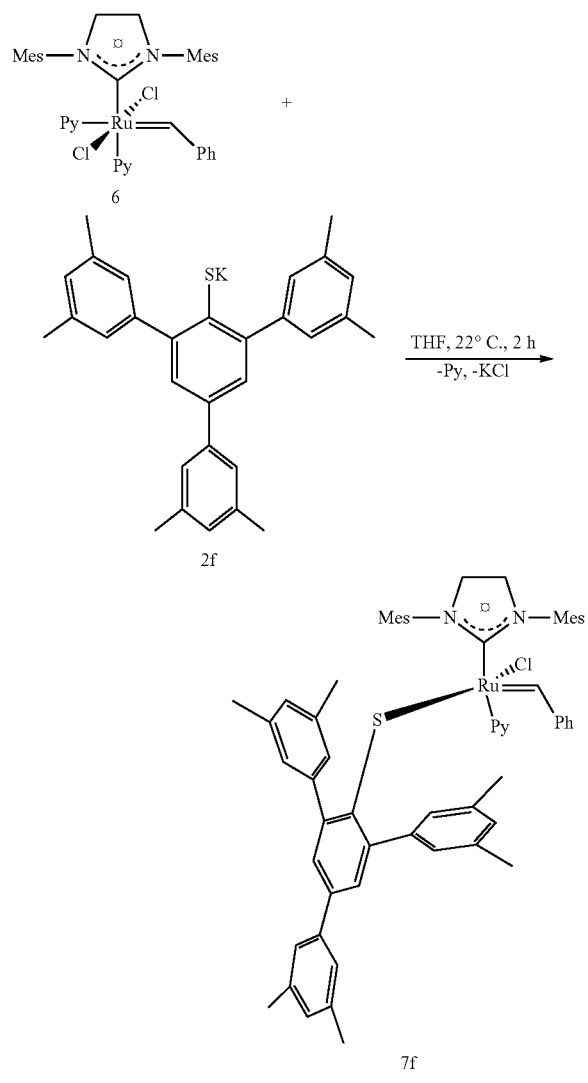

In a glovebox, a 25 mL vial, equipped with a magnetic stirring bar and a screw cap, was charged with complex 6 (80 mg, 0.112 mmol), potassium 2,4,6-tris(3,5-dimethylphenyl) benzenethiolate (58 mg, 0.125 mmol) 2f, and tetrahydrofuran (4 mL). After the addition of the solvent the color of the suspension changed rapidly from green to reddish-brown. The mixture was stirred at room temperature for two hours. The solvent was removed under reduced pressure. The residual was dissolved in a minimum amount of toluene (about 1 mL), then 3 mL of pentane were added and the resulting dark-brown mixture was rapidly filtered through celite. The filtrate was placed in the freezer (−32° C.) for a couple of days. The red-brown micro-crystalline solid was isolated, washed three times with pentane and dried in the glove box to give 70 mg (56%) of 7f. $C_5H_{12}$. $^1$H NMR (600.17 MHz, $C_6D_6$): δ=18.54 (s, 0.91H), 17.04 (s, 0.09H), 8.66-5.56 (m, 23H), 3.47-3.35 (m, 0.91H), 3.27-3.10 (m, 2H), 3.10-3.00 (m, 1.09H), 2.98 (s, 2.73), 2.69 (s, 2.73H), 2.63-2.25 (m, 20.59H), 2.23 (s, 0.54H), 2.15 (0.54H), 2.07 (s, 0.54H), 2.02 (s, 5.5H), 1.63 (s, 2.73H). $^{13}$C{$^1$H} NMR (150.91 MHz, $C_6D_6$): δ=302.05, 301.63, 287.22, 215.14, 207.65, 153.43 (br), 151.87, 151.65, 151.35, 145.55, 145.01, 143.73, 141.13, 141.09, 139.83, 139.13, 138.63, 138.07, 137.89, 137.45, 137.19, 136.99, 136.63 (br), 136.40, 136.12, 135.90, 135.77, 134.31, 131.83, 131.40 (br), 130.40, 129.79, 129.58, 129.24, 129.09, 128.69, 128.35, 127.46, 126.65, 124.99, 124.66, 122.64, 51.78, 51.29, 50.44, 22.22, 21.86, 21.46, 21.41, 21.36, 21.20, 20.57, 19.54, 19.51, 19.07, 17.76. Elemental analysis, calculated for $C_{63}H_{66}ClN_3RuS$: C, 73.19; H, 6.43; N, 4.06; found: C, 73.56; H, 6.49; N, 3.80. HRMS (DART): calculated for $C_{58}H_{61}{}^{35}ClN_2{}^{101}RuS$ [M−py]$^+$: m/z=953.3300, found: m/z=953.3293.

EXAMPLE 8

Preparation of Ruthenium Complex 9a

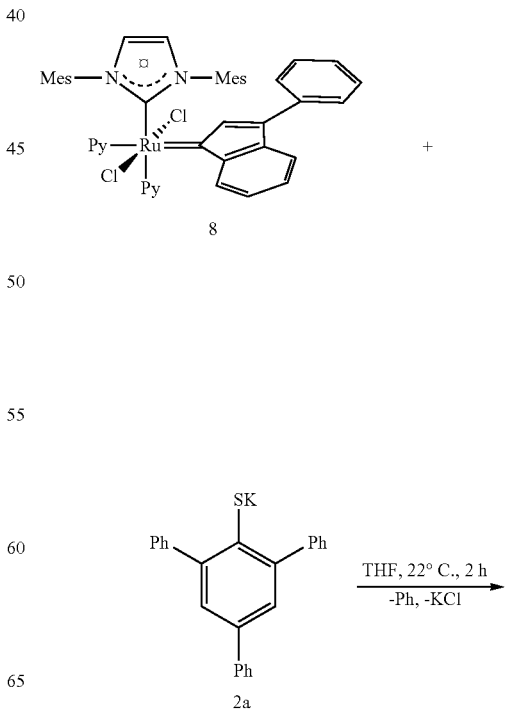

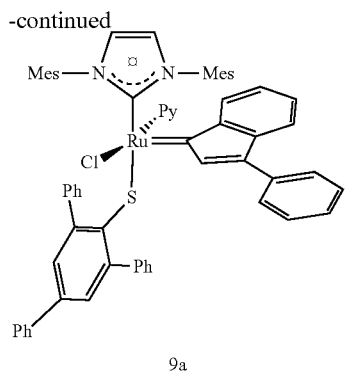

9a

In a glovebox, a 25 mL vial, equipped with a magnetic stirring bar and a screw cap, was charged with complex 8 (100 mg, 0,121 mmol), potassium 2,4,6-triphenylbenzenethiolate (47.6 mg, 0,126 mmol) 2a, and tetrahydrofuran (5 mL). The mixture was stirred at room temperature for 2 hours, and then it was filtered through a short pad of celite. The filtrate was concentrated under reduced pressure to about 2 mL. Then 3 mL of pentane was slowly added to the solution and the vial was placed overnight in a freezer at −32° C. The dark red microcrystals (92 mg, yield 72%) were collected by decantation, washed three times with pentane and dried in the glove box to give 92 mg (72%) of 9a. $^1$H NMR (600.17 MHz, CDCl$_3$): δ=8.62 (br s, 0.32H), 8.48 (br d, $^3J_{HH}$=5.2, 0.68H), 8.13 (br d, $^3J_{HH}$=7.2, 1.36H), 7.88 (br d, $^4J_{HH}$=1.4, 0.32H), 7.79-7.27 (m, 15.2H), 7.24-6.73 (m, 9.90H), 6.54 (br d, $^3J_{HH}$=5.2, 0.64H), 6.47 (br d, $^3J_{HH}$=5.9, 0.32H), 6.45-6.37 (m, 1.36H), 6.36-6.23 (m, 1.62H), 6.17 (s, 1.36H), 6.06-5.89 (m, 2.0H), 5.81 (t, $^3J_{HH}$=5.9, 0.32H), 5.76 (d, $^3J_{HH}$=8.0, 0.32H), 6.45-6.37 (m, 1.36H), 6.36-6.23 (m, 1.62H), 6.17 (s, 1.36H), 6.05-5.88 (m, 2.0H), 5.81 (t, $^3J_{HH}$=5.9, 0.32H), 5.76 (d, $^3J_{HH}$=8.0, 0.32H), 5.29-5.20 (m, 1.0H, 5.18 (t, $^3J_{HH}$=5.9, 0.32H), 5.10 (s, 0.32H), 4.15 (t, $^3J_{HH}$=5.9, 0.32H), 2.38 (s, 2.04H), 2.33 (s, 0.96H), 2.31 (s, 2.04H), 2.23 (s, 0.96H), 2.21 (s, 2.04H), 2.16 (s, 0.96H), 2.08 (s, 0.96H), 2.08 (s, 0.96H), 2.06 (s, 0.96H), 1.66 (s, 2.04H), 1.63 (s, 0.96H), 1.58 (s, 2.04H), 1.02 (s, 2.04H). $^{13}$C{$^1$H} NMR (150.91 MHz, CDCl$_3$): δ=270.77, 183.31, 180.30, 159.11, 154.03, 150.03, 149.76, 147.98, 147.61, 146.70, 145.50, 145.15, 142.85, 142.82, 142.70, 141.54, 141.13, 140.49, 140.10, 139.64, 139.59, 139.15, 139.05, 138.77, 138.58, 138.04, 137.34, 137.25, 137.09, 137.04, 136.79, 136.67, 136.00, 135.96, 135.90, 135.47, 134.62, 134.55, 134.09, 133.76, 133.69, 132.97, 131.96, 130.75, 130.34, 130.01, 129.88, 129.73, 129.51, 129.44, 129.27, 129.22, 129.14, 129.09, 128.68, 128.44, 128.36, 128.23, 128.06, 127.87, 127.72, 127.65, 127.60, 127.45, 127.28, 127.14, 126.92, 126.82, 126.68, 126.55, 126.47, 126.35, 126.28, 125.88, 125.77, 125.58, 125.35, 125.31, 125.11, 124.38, 124.33, 123.98, 123.85, 123.41, 122.48, 121.56, 117.38, 99.74, 93.89, 90.90, 89.47, 87.80, 78.93, 63.76, 21.21, 21.14, 20.96, 20.90, 20.80, 20.16, 20.02, 19.85, 19.57, 18.60, 18.42, 18.23.

EXAMPLE 9

Preparation of Ruthenium Complex 11f

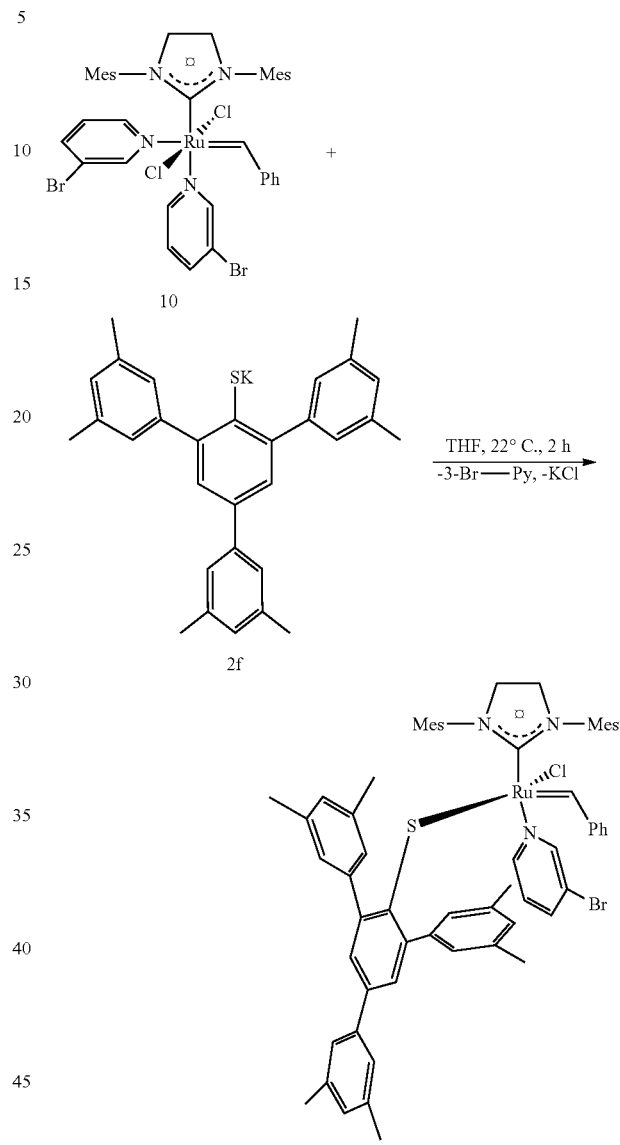

In a glovebox, a 25 mL vial, equipped with a magnetic stirring bar and a screw cap, was charged with complex 10 (50 mg, 0.057 mmol), potassium 2,4,6-tris(3,5-dimethylphenyl)benzenethiolate (26 mg, 0.057 mmol) 2f, and toluene (4 mL). After the addition of the solvent the color of the suspension changed rapidly from green to reddish-brown. The mixture was stirred at room temperature for two hours and then filtered through celite. The solvent was removed under reduced pressure to give 58 mg (92%) of 11f. $^1$H NMR (500.13 MHz, C$_6$D$_6$): δ=18.41 (s, 0.58H), 17.00 (s, 0.42H), 8.62 (br s, 0.84H), 8.19 (br s, 0.84H), 7.61-7.54 (br m, 0.84H), 7.45-7.26 (br m, 0.84H), 7.29-7.24 (br m, 1H), 7.20-7.18 (br, 1H), 7.07-7.04 (br m, 0.84H), 6.98-6.63 (br m, 15.82H), 6.37 (br s, 0.84H), 6.26 (br s, 0.58H), 5.61 (br s, 0.58H), 3.61-3.00 (br m, 4H), 2.93 (br s, 1.74H), 2.66 (br s, 1.74H), 2.53-2.35 (br m, 14.22H), 2.30 (br s, 1.26H), 2.29 (br s, 1.74H), 2.25-2.21 (br s, 2.52H), 2.17 (s, 1.26H), 2.15

(s, 1.26H), 2.11 (s, 3.78H), 2.08 (br s, 1.26H), 2.00 (br s, 3.48H), 1.60 (br s, 1.74H). $^{13}C\{^1H\}$ NMR (150.91 MHz, $C_6D_6$): δ=302.12, 214.30, 153.12, 152.02, 151.54, 151.37, 149.70, 148.06, 145.60, 144.82, 142.91, 142.27, 142.06, 140.98, 140.04, 139.03, 138.08, 137.58, 137.36, 137.15, 136.65, 135.36, 131.65, 130.40, 129.63, 129.33, 129.27, 129.23, 129.17, 128.77, 128.35, 127.66, 125.16, 124.72, 123.56, 118.40, 51.83, 51.43, 50.35, 22.13, 21.54, 21.43, 21.37, 21.34, 20.51, 19.56, 19.03, 17.72. HRMS (ESI$^+$): calculated for $C_{58}H_{62}N_2{}^{102}RuS$ [M−3Br−Py−Cl+H]$^+$: m/z=920.36772, found: m/z=920.36851.

EXAMPLE 10

Preparation of Ruthenium Complex 13f

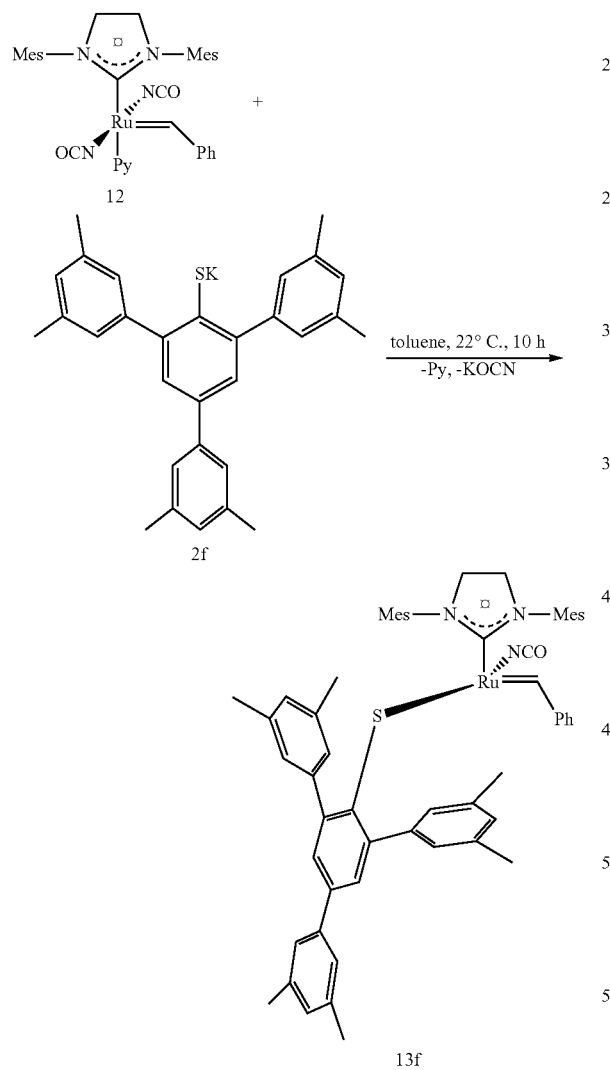

In a glovebox, a 25 mL vial, equipped with a magnetic stirring bar and a screw cap, was charged with complex 12 (50 mg, 0.076 mmol), potassium 2,4,6-tris(3,5-dimethylphenyl)benzenethiolate (35 mg, 0.076 mmol) 2f, and toluene (2 mL). The mixture was stirred for 10 hours at room temperature. The mixture was filtered through a pad of celite. The solvent was reduced by half under vacuum and then pentane (about 5 mL) was slowly added until the solution became slightly cloudy. The mixture was placed in the freezer (−32° C.) for a couple of days. The brown microcrystals were isolated, washed three times with pentane and dried under vacuum to give 18 mg (25%) of 13f. $^1H$ NMR (600.17 MHz, $C_6D_6$): δ=17.46 (s, 1H), 7.92 (br d, $^3J_{HH}$=7.7 Hz, 2H), 7.75 (br s, 3H), 7.28 (br tt, $^3J_{HH}$=7.4 Hz, $^4J_{HH}$=1.1 Hz, 1H), 7.22 (s, 2H), 7.07 (br s, 1H), 7.01 (br dd, $^3J_{HH}$=8.1 Hz, $^4J_{HH}$=7.4 Hz, 2H), 6.96 (br s, 1H), 6.93 (br s, 1H), 6.83-6.02 (m, 7H), 3.09-2.90 (m, 4H), 2.51-2.34 (m, 12H), 2.31-215 (m, 9H), 2.08 (s, 6H), 2.04 (s, 6H), 1.54 (br s, 3H). $^{13}C\{^1H\}$ NMR (150.91 MHz, $C_6D_6$): 302.11, 210.36, 151.98, 149.54, 147.96, 145.98, 144.14, 143.68, 141.16, 140.66, 138.67, 138.49, 138.12, 138.07, 136.83, 135.75, 134.91, 131.83, 131.07, 129.97, 129.93, 129.64, 128.90, 128.59, 128.46, 128.35, 124.91, 124.74, 114.06, 50.84, 22.32, 21.77, 21.40, 21.20, 21.02, 19.36, 18.76. HRMS (ESI$^+$): calculated for $C_{58}H_{62}N_2{}^{102}RuS$ [M−NCO+H]$^+$: m/z=920.36772, found: m/z=920.36701.

EXAMPLE 11

Preparation of Ruthenium Complex 14g

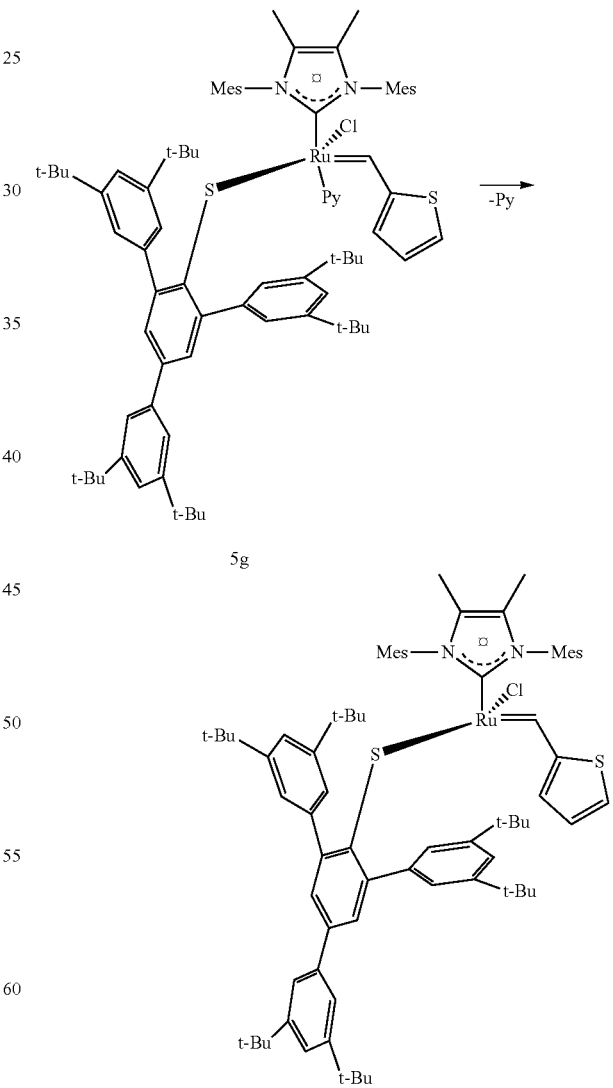

In a glovebox, a 25 mL vial, equipped with a magnetic stirring bar and a screw cap, was charged with complex 5g (22 mg, 0.017 mmol) and pentane (5 mL). The mixture was stirred for a few minutes in such a way to achieve a dark-brown solution. Then 250 mg of activated basic alumina was added to the vial and the mixture was stirred for about 30 minutes. During this time the basic alumina becomes brown and the pentane solution becomes pale yellow-brown in color. The solution was removed with a Pasteur pipette and the basic alumina was washed five times with about 5 mL of pentane by following this procedure: The impregnated alumina and pentane were stirred for a few minutes until the pentane extract became slightly colored of pale yellow-brown, the stirring was stopped and the mixture was decanted. Then the pentane solution was removed with a Pasteur pipette.

After this treatment, the brown colored alumina was extracted three times with about 2 mL of toluene. The dark-brown solution was filtered through a glass-fiber paper and solvent was removed under vacuum to give 12 mg (58%) of 14g. $^1$H NMR (600.17 MHz, $C_6D_6$): δ=17.35 (s, 1H), 8.14 (br s, 2H), 7.89 (br s, 1H), 7.69 (br dt, $^3J_{HH}$=4.9 Hz, $^4J_{HH}$=1.1 Hz, 1H), 7.60 (br s, 1H), 7.57 (br d, $^4J_{HH}$=1.8 Hz, 2H), 7.52 (br s, 1H), 7.55 (br m, 1H), 7.44 (br t, $^4J_{HH}$=1.8 Hz, 1H), 7.02 (br s, 1H), 6.91 (br s, 1H), 6.80 (br s, 1H), 6.69 (s, 2H), 6.66 (br dd, $^3J_{HH}$=4.9 Hz, $^3J_{HH}$=4.9 Hz, $^3J_{1\text{-}iii}$=4.9 Hz, 1H), 6.63 (br, 2H), 2.34 (s, 6H), 2.15 (s, 6H), 2.07 (s br, 6H), 1.50 (s, 27H), 1.28 (s, 6H), 1.25 (s, 18H), 0.97 (br, 1H), 0.90 (br s, 9H). $^{13}C\{^1H\}$ NMR (150.91 MHz, $C_6D_6$): 276.97, 174.63, 166.23, 157.00, 156.64, 151.09, 150.83, 149.71, 146.60, 143.89, 141.60, 138.78, 138.40, 138.24, 138.13, 136.93, 133.69, 133.39, 130.64, 129.79, 129.45, 128.35, 127.61, 127.27, 125.54, 124.09, 121.90, 120.53, 120.32, 111.75, 35.54, 35.19, 34.94, 32.01, 31.61, 30.20, 21.23, 20.14, 19.62, 9.05.

EXAMPLE 12

Homocoupling of Neat Allylbenzene

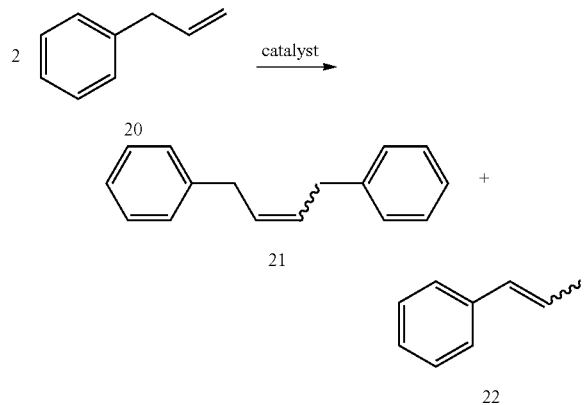

In a glove box, a 4 mL vial equipped with a magnetic stirring bar was charged with 59 mg (0.50 mmol) of allylbenzene and the catalyst (0.005 mmol, 1 mol %). The reaction mixture was stirred at room temperature (22° C.) for five minutes (open atmosphere). The reaction was quenched by filtration through silica gel using hexane as eluent. Determination of conversions, yields, and Z-selectivities were done according to literature procedures. (20, 28)

| entry | cat. | 21/22[a] | Yield of 21[b] | % Z-21[a] |
|---|---|---|---|---|
| 1 | 5e | 48 | 64 | 66 |
| 2 | 5f | >100 | 73 | 80 |
| 3 | 5g | 9 | 28 | 86 |
| 4 | 5a | 63 | 69 | 63 |
| 5 | 7a | 15 | 41 | 81 |
| 6 | 7f | 51 | 33 | 86 |
| 7 | 9a | >100 | 8 | 83 |
| 8 | 11f | >100 | 50 | 75 |
| 10 | 13f | 6 | 67 | 68 |
| 11 | 14g | >100 | 31 | 79 |
| 12 | D1-4d[c] | 0.2 | 2 | 83 |
| 13 | D2-4a[c] | 0.6 | 3 | 87 |

[a]Determined by $^1$H NMR.
[b]Isolated yield.
[c]See FIG. 2 for the Lewis structure and literature references.

EXAMPLE 13

Homocoupling of Neat Terminal Olefin with Catalyst 5f

In a glove box, a 4 mL vial equipped with a magnetic stirring bar and a screw cap was charged with 0.50 mmol of substrate, 2 mg of hexamethylbenzene (internal standard) and the catalyst (0.005 mmol, 1 mol %). The vial was closed and the reaction mixture was stirred at room temperature (22° C.) for five minutes. The reaction was quenched with an excess of ethyl vinyl ether. Determination of conversions, yields, and Z-selectivities were done according to literature procedures. (20, 28)

| entry | substrate | % conv.[a] | % yield[a] | % Z[a] |
|---|---|---|---|---|
| 1 | 1-octene | 68 | 68 | 79 |
| 2 | allylacetate | 46 | 46 | 80 |
| 3 | 4-phenyl-1-butene | 76 | 75 | 79 |
| 4 | allyl boronic acid pinacol ester | 61 | 53 | 94 |
| 5 | N-allylanyline | 14 | 14 | 75 |
| 6 | 2-allyloxyethanol | 2 | 2 | 78 |

[a]Determined by $^1$H NMR.

EXAMPLE 14

Homocoupling of Terminal Olefins in Toluene Solution (1 M) at Room Temperature

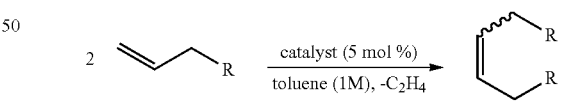

Reactions under ambient pressure: In a glove box, a 4 mL vial equipped with a magnetic stirring bar and a screw cap was charged with the substrate (0.1 mmol) and 2 mg of hexamethylbenzene (internal standard). Then a solution of the catalyst (5×10$^{-3}$ mmol, 5 mol %) dissolved in the right amount of toluene to achieve the final concentration of 1 M in substrate, was added to the vial containing the substrate and the internal standard. The vial was closed and the reaction mixture was stirred at room temperature (22° C.). Samples (about 10 μL) of the reaction mixture were withdrawn at regular time intervals, and quenched with an excess of ethyl vinyl ether. Determination of conversions, yields, and Z-selectivities were carried out by comparing the integrals of the peaks due to the olefinic protons of substrates and products, identified by comparison with literature data, (20, 37-41) with that of the internal standard.

Reactions under static vacuum: In a glove box, a 50 mL Schlenk flask equipped with a Young's tap and a magnetic stirring bar was charged with the substrate (0.1 mmol) and 2 mg of hexamethylbenzene (internal standard). Then a solution of the catalyst ($5 \times 10^{-3}$ mmol, 5 mol %) dissolved in the right amount of toluene to achieve the final concentration of 1 M in substrate, was added to the flask. The flask was closed, exported outside the glovebox, and the mixture was immediately frozen in liquid nitrogen. The flask was then evacuated to about $10^{-2}$ mbar and closed, allowed to heat to room temperature and stirred. Samples (about 10 μL) of the reaction mixture were withdrawn at regular time intervals, and quenched with an excess of ethyl vinyl ether. In order to take a sample, the progress of the reaction was stopped by cooling the reaction mixture with liquid nitrogen, and the flask was backfilled with argon. Then the static vacuum was restored by using the same procedure described above. Determination of conversions, yields, and Z-selectivities were carried out by comparing the integrals of the peaks due to the olefinic protons of substrates and products, identified by comparison with literature data, (20, 37-41) with that of the internal standard.

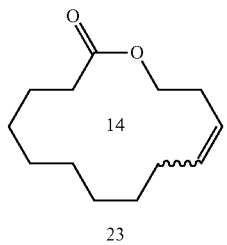

23

Reactions under ambient pressure: In a glove box, a 25 mL vial, equipped with a magnetic stirring bar and a screw cap, was charged with 3 mg (0.0126 mmol) of diene 22, 1.5 mg of hexamethylbenzene (internal standard) and about 90% of the total amount of toluene. In a different vial 5f was dissolved with the remaining amount of toluene and the resulting solution was transferred to the first vial. The vial was closed and the mixture was stirred at room temperature (22° C.). Samples (0.5 mL) of the reaction mixture were withdrawn at regular time intervals, and quenched with an excess of ethyl vinyl ether, the solvent was removed by vacuum, and the residual was analyzed by $^1$H NMR (600 MHz and 850 MHz). Determination of conversions, yields,

| entry | substrate | cat. | pressure, mbar | time, minutes | % conv$^a$ | yield$^a$ | % Z$^a$ |
|---|---|---|---|---|---|---|---|
| 1 | 10-undecenoic acid | 5f | 1 | 5 | 50 | 50 | 66 |
|   |   |   |   | 10 | 56 | 56 | 57 |
| 2 | 10-undecenoic acid | 5f | $1 \cdot 10^{-2}$ | 5 | 59 | 56 | 67 |
| 3 | 10-undecenoic acid | 7f | $1 \cdot 10^{-2}$ | 5 | 34 | 28 | 45 |
| 4 | 10-undecenoic acid | 5g | $1 \cdot 10^{-2}$ | 5 | 33 | 28 | 35 |
| 5 | 10-undecenoic acid | 13f | $1 \cdot 10^{-2}$ | 5 | 74 | 15 | 24 |
| 6 | 10-undecenoic acid | D2-4a$^b$ | 1 | 5 | 4 | <1 | n.d |
| 7 | 10-undecenoic acid | D2-4a$^b$ | $1 \cdot 10^{-2}$ | 5 | 10 | <1 | n.d. |
| 8 | 4-pentenoic acid | 5f | 1 | 5 | 43 | 30 | 69 |
|   |   |   |   | 10 | 50 | 32 | 54 |
| 9 | 4-pentenoic acid | 5f | $1 \cdot 10^{-2}$ | 5 | 35 | 35 | 79 |
|   |   |   |   | 25 | 44 | 42 | 70 |
|   |   |   |   | 60 | 50 | 42 | 54 |
| 10 | 4-pentenoic acid | GII$^c$ | $1 \cdot 10^{-2}$ | 25 | 17 | 17 | 11 |
|   |   |   |   | 60 | 46 | 45 | 8 |
| 11 | 2-Allyloxyethanol | 5f | 1 | 5 | 50 | 50 | 52 |
| 12 | 2-Allyloxyethanol | 7f | 1 | 5 | 48 | 35 | 57 |
| 13 | 2-Allyloxyethanol | D2-4a$^b$ | 1 | 5 | 0 | 0 | — |

$^a$Determined by $^1$H NMR (Internal Standard = hexamethylbenzene).
$^b$See FIG. 2 for the Lewis structure and literature references.
$^c$GII = Grubbs second generation catalyst.

EXAMPLE 15

Ring Closing Metathesis of Diene 22

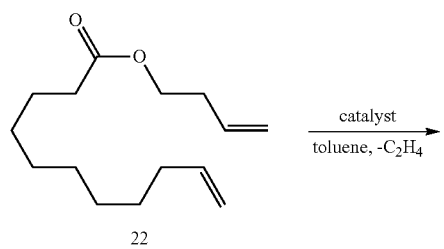

22 and Z-selectivities were obtained from the analysis of 600 and 850 MHz $^1$H NMR spectra. (24, 42)

| entry | cat. | cat. load, mol % | sub. conc. (mM) | T (° C.) | time, hours | % conv.$^a$ | yield$^a$ | % Z$^a$ |
|---|---|---|---|---|---|---|---|---|
| 1 | 5f | 10 | 3 | 22 | 1 | 70 | 19 | 74 |
|   |   |   |   |   | 2 | 75 | 38 | 70 |
|   |   |   |   |   | 4 | 81 | 62 | 53 |
|   |   |   |   |   | 9 | 88 | 71 | 42 |
|   |   |   |   |   | 22 | 92 | 77 | 30 |
| 2 | 5f | 10 | 1 | 22 | 2 | 48 | 41 | 73 |
|   |   |   |   |   | 8 | 71 | 57 | 63 |
|   |   |   |   |   | 22 | 81 | 72 | 48 |
| 3 | 5f | 20 | 1 | 22 | 2 | 59 | 52 | 68 |
|   |   |   |   |   | 4 | 69 | 62 | 58 |
|   |   |   |   |   | 8 | 79 | 72 | 47 |
|   |   |   |   |   | 22 | 95 | 88 | 41 |

-continued

| entry | cat. | cat. load, mol % | sub. conc. (mM) | T (° C.) | time, hours | % conv.[a] | % yield[a] | % Z[a] |
|---|---|---|---|---|---|---|---|---|
| 4[b] | 5f | 10 | 1 | 100 | 0.33 | 62 | 49 | 73 |
|  |  |  |  |  | 1 | 87 | 64 | 64 |
|  |  |  |  |  | 1.5 | 91 | 69 | 63 |
| 5 | 7f | 10 | 3 | 22 | 1 | 51 | 17 | 80 |
| 6 | 9a | 10 | 3 | 22 | 1 | 64 | 33 | 58 |
|  |  |  |  |  | 22 | 86 | 53 | 57 |
| 7 | D1-4d[c] | 10 | 3 | 22 | 1 | 86 | 2 | 68 |
| 8 | D2-4a[c] | 10 | 3 | 22 | 1 | 81 | 0 | — |
| 9 | GII[d] | 10 | 3 | 22 | 1 | 85 | 67 | 10 |

[a]Determined by analysis of 600 and 850 MHz ¹H NMR spectra of unpurified mixtures (internal standard hexamethylbenzene).
[b]The reaction was carried out in a 300 mL Schlenk flask equipped with a Young's tap. The reaction mixture was prepared inside a glove box, the flask was closed, exported in a fume hood and connected to a Schlenk line, and then heated at 100° C. in a preheated oil bath and stirred.
[c]See FIG. 2 for the Lewis structure and literature references.
[d]GII = Grubbs second generation catalyst.

Reactions at 60° C. and Under Static Vacuum ($10^{-2}$ Mbar): In a glove box, a 50 mL Schlenk flask equipped with a Young's tap and a magnetic stirring bar was charged with 3 mg (0.0126 mmol) of diene 22, 1.5 mg of hexamethylbenzene (internal standard) and about 90% of the total amount of toluene. In a different vial the catalyst (0.00126 mmol) was dissolved with the remaining amount of toluene and the resulting solution was transferred to the flask. The flask was closed, exported outside the glovebox, and the mixture was immediately frozen in liquid nitrogen. The flask was then evacuated to about $10^{-2}$ mbar and closed, heated first by immersion in a tepid water bath and then heated at 60° C. in a preheated oil bath or immersed in an ice-water bath and stirred. Samples (0.5 mL) of the reaction mixture were withdrawn at regular time intervals, and quenched with an excess of ethyl vinyl ether, the solvent was removed by vacuum, and the residual was analyzed by ¹H NMR (600 MHz and 850 MHz). Determination of conversions, yields, and Z-selectivities were obtained from the analysis of 600 and 850 MHz ¹H NMR spectra. (24, 42)

| entry | cat. | cat. load, mol % | sub. conc. (mM) | T (° C.) | time, hours | % conv.[a] | yield[a] (isol)[b] | % Z[a] |
|---|---|---|---|---|---|---|---|---|
| 1[b] | 5f | 10 | 3 | 60 | 2 | 94 | 71 (56) | 54 (57)[c] |
| 2 | 5g | 10 | 3 | 60 | 2 | 75 | 10 | 60 |
| 3 | 7f | 10 | 3 | 60 | 2 | 65 | 23 | 72 |
| 4 | D1-4d[d] | 10 | 3 | 60 | 2 | 89 | <1 | n.d. |
| 5 | D2-4a[d] | 10 | 3 | 60 | 2 | 77 | 0 | — |
| 6 | 5f | 5 | 10 | 0 | 2 | 25 | 8 | 72 |

[a]Determined by analysis of 600 and 850 MHz ¹H NMR spectra of unpurified mixtures (internal standard hexamethylbenzene).
[b]The reaction was carried out in a 300 mL Schlenk flask and on a larger scale (0.20 mmol of diene 22). The product was isolated by column chromatography on silica gel using pentane/diethyl ether (92:8) as eluent.
[c]Determined by analysis of 600 MHz ¹H NMR spectrum of the isolated product.
[d]See FIG. 2 for the Lewis structure and literature references.

EXAMPLE 16

Ring Closing Metathesis of Diene 24

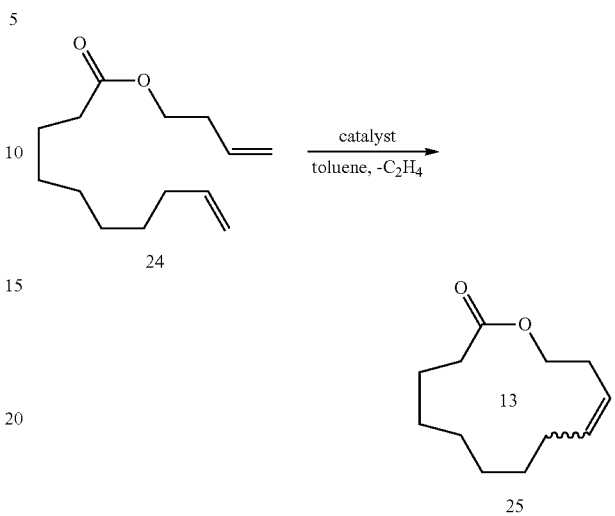

In a glove box, a 300 mL Schlenk flask, equipped with a magnetic stirring bar, was charged with the diene 24 (0.126 mmol), then 120 mL (i.e. about 95 of the total amount of solvent to prepare a 1 mM solution) was added to the flask. In a vial 5f (0.0126 mmol) was dissolved in 6 ml (i.e. the remaining amount of solvent to prepare a 1 mM solution) of toluene and the resulting solution was transferred to the Schlenk flask. The flask was closed, exported outside the glovebox, and the mixture was immediately frozen in liquid nitrogen. The flask was then evacuated to about $10^{-2}$ mbar and closed, heated first by immersion in a tepid water bath and then heated at 100° C. in a preheated oil bath and stirred for one hour. The reaction was quenched with an excess of ethyl vinyl ether, the solvent was removed by vacuum, and the product 25 was isolated by column chromatography on silica gel using pentane/diethyl ether (85:15) as eluent. Determination of Z-selectivities were obtained from the analysis of 600 ¹H NMR spectra.

| entry | cat. | cat. load, mol % | sub. conc. (mM) | T (° C.) | time, hours | % conv.[a] | % yield[b] | % Z[c] |
|---|---|---|---|---|---|---|---|---|
| 1 | 5f | 10 | 1 | 100 | 1 | 94 | 56 | 57 |

[a]Determined by analysis of 600 MHz ¹H NMR spectrum of unpurified mixture.
[b]Isolated yield.
[c]Determined by analysis of 600 MHz ¹H NMR spectrum of the isolated product.

REFERENCES (1) Hoveyda, A. H.; Zhugralin, A. R., *Nature* 2007, 450, 243;
(2) Grubbs, R. H., *Adv. Synth. Catal.* 2007, 349, 23 and 34;
(3) Thayer, A. M., *Chem. Eng. News* 2007, 85, 37;
(4) Fürstner, A.; Mathes, C.; Lehmann, C. W., *Chem. Eur. J.* 2001, 7, 5299;
(5) Gradillas, A.; Perez-Castells, J., *Angew. Chem. Int. Ed.* 2006, 45, 8086;
(6) Fürstner, A.; Langemann, K., *Synthesis-Stuttgart* 1997, 792;
(7) Fürstner, A.; Guth, O.; Rumbo, A; Seidel, G., *J. Am. Chem. Soc.* 1999, 121, 11108;

(8) Jakubec, P.; Cockfield, D. M.; Dixon, D. J., *J. Am. Chem. Soc.* 2009, 131, 16632;
(9) Trnka, T. M.; Grubbs, R. H., *Acc. Chem. Res.* 2001, 34, 18;
(10) Lee, C. W.; Grubbs, R. H., *Org. Lett.* 2000, 2, 2145;
(11) Malcolmson, S. J.; Meek, S. J.; Sattely, E. S.; Schrock, R. R.; Hoveyda, A. H., *Nature* 2008, 456, 933;
(12) Ibrahem, I.; Yu, M.; Schrock, R. R.; Hoveyda, A. H., *J. Am. Chem. Soc.* 2009, 131, 3844;
(13) Flook, M. M.; Jiang, A. J.; Schrock, R. R.; Muller, P.; Hoveyda, A. H., *J. Am. Chem. Soc.* 2009, 131, 7962;
(14) Peryshkov, D. V.; Schrock, R. R.; Takase, M. K.; Müller, P.; Hoveyda, A. H. *J. Am. Chem. Soc.* 2011, 133, 20754.
(15) Jiang, A. J.; Zhao, Y.; Schrock, R. R.; Hoveyda, A. H., *J. Am. Chem. Soc.* 2009, 131, 16630;
(16) Meek, S. J.; O'Brien, R. V.; Llaveria, J.; Schrock, R. R.; Hoveyda, A. H. *Nature* 2011, 471, 461.
(17) Yu, M.; Wang, C.; Kyle, A. F.; Jakubec, P.; Darren J. Dixon, D. J.; Schrock, R. R.; Hoveyda, A. H. *Nature* 2011, 479, 88.
(18) Wang, C.; Haeffner, F.; Schrock, R. R.; Hoveyda, A. H. *Angew. Chem. Int. Ed.* 2013, 52, 1939.
(19) Endo, K.; Grubbs, R. *H. J. Am. Chem. Soc.* 2011, 133, 8525.
(20) Keitz, B. K.; Endo, K.; Herbert, M. B.; Grubbs, R. *H. J. Am. Chem. Soc.* 2011, 133, 9686.
(21) Keitz, B. K.; Endo, K.; Patel, P. R.; Herbert, M. B.; Grubbs, R. H. *J. Am. Chem. Soc.* 2012, 134, 693.
(22) Keitz, B. K.; Fedorov, A.; Grubbs, R. *H. J. Am. Chem. Soc.* 2012, 134, 2040.
(23) Rosebrugh, L. E.; Marx, V. M.; Keitz, B. K.; Grubbs, R. H. *J. Am. Chem. Soc.* 2013, 135, 10032.
(24) Marx, V. M.; Herbert, M. B.; Keitz, B. K.; Grubbs, R. H. *J. Am. Chem. Soc.* 2013, 135, 94.
(25) Rosebrugh, L. E.; Herbert, M. B.; Marx, V. M.; Keitz, B. K.; Grubbs, R. H. *J. Am. Chem. Soc.* 2013, 135, 1276.
(26) Hartung, J.; Grubbs, R. H. *J. Am. Chem. Soc.,* 2013, 135, 10183.
(27) Jensen, V. R.; Occhipinti, G.; Hansen, F. Novel Olefin Metathesis Catalysts. Int. Patent Appl. WO 2012/032131, 2012.
(28) Occhipinti, G.; Hansen, F.; Törnroos, K. W.; Jensen, V. R. *J. Am. Chem. Soc.,* 2013, 135, 3331.
(29) R. Kashif M. Khan, R. K. M.; Torker, S.; Hoveyda, A. H. *J. Am. Chem. Soc.,* 2013, 135, 10258.
(30) Kumar, P. S.; Wurst, K.; Buchmeiser, M. R. *Chem. Asian J.* 2009, 4, 1275.
(31) Merino, E.; Poli, E.; Díaz, U.; Brunel, D. Dalton Trans., 2012, 41, 10913.
(32) Occhipinti, G.; Koudriavtsev, V.; Törnroos, K. W., Jensen, V. R. Dalton Trans., 2014, 43, 11106.
(33) S. E. Lehman Jr, J. E. Schwendeman, P. M. O'Donnell, K. B. Wagener, *Inorg. Chim. Acta* 2003, 345, 190.
(34) D. Bourgeois, A. Pancrazi, S. P. Nolan, J. Prunet, *J. Organomet. Chem.* 2002, 643-644, 247.
(35) S. H. Hong, D. P. Sanders, C. W. Lee, R. H. Grubbs, *J. Am. Chem. Soc.* 2005, 127, 17160.
(36) P. A. Fokou, M. A. R. Meier, *Macromol. Rapid Commun.* 2010, 31, 368.
(37) Martin T. Mwangi, M. T.; Runge, B.; Bowden, N. B. *J. Am. Chem. Soc.,* 2006, 128, 14434.
(38) Sobhi, H. F.; Minkler, P. E.; Hoppel, C. L. *Anal. Biochem.,* 2010, 401, 114.
(39) Kusuma, B. R.; Peterson, L. B.; Zhao, H.; Vielhauer, G.; Holzbeierlein, J.; Blagg, B. S. J. *J. Med. Chem.,* 2011, 54, 6234.
(40) Burlison, J. A.; Blagg, B. S. J. *Org. Lett.,* 2006, 8, 4855.
(41) Matson, J. B.; Grubbs, R. H. *Macromolecules,* 2010, 43, 213.
(42) Wang, C.; Yu, M.; Kyle, A. F.; Jakubec, P.; Dixon, D. J.; Schrock, R. R.; Hoveyda, A. H. *Chem. Eur. J.* 2013, 19, 2726.
(43) Sanford, M. S.; Love, J. A.; Grubbs, R. H. *Organometallics* 2001, 20, 5314-5318.
(44) Clavier, H.; and S. P. Nolan, in Metathesis Chemistry, ed.Y. Imamoglu and V. Dragutan, NATO ASI Series, Dordrecht, 2007, vol. 243, pp. 29-37.
(45) Buchmeiser, M. R.; Ahmad, I.; Gurram, V.; Kumar, P. S. *Macromolecules* 2011, 44, 4098-4106.
(46) Fulmer, G. R.; Miller, A. J. M.; Sherden, N. H.; Gottlieb, H. E.;
(47) *Novel Olefin Metathesis Catalysts.* Jensen, V. R.; Occhipinti, G.; Hansen, F. R. U.S. Pat. No. 8,716,488 B2, May 6, 2014.
(48) *Novel Organometallics Catalysts.* Jensen, V. R.; Occhipinti, G U.S. Pat. No. 9,303,100 B2, Apr. 5, 2016.
(49) Williams, J. E.; Harner, M. J.; Sponsler, M. B. *Organometallics* 2005, 24, 2013.
(50) Romero, P. E.; Piers, W. E.; McDonald, R. *Angew. Chem. Int. Ed.* 2004, 43, 6161.

The invention claimed is:

1. A compound having the general Formula (I):

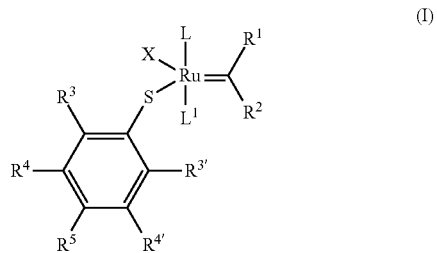

(I)

wherein

L is an N-heterocyclic carbene ligand, $L^1$ is pyridine, that may optionally be substituted with one or more substituents, —NCO, —CN, —CNO, —NCS, —$N_3$, X is halide, —NCO, —CN, —CNO, —NCS, or —$N_3$, $R^1$ and $R^2$ are independently selected from the group consisting of H, $C_{1-20}$ alkyl, $C_{2-20}$ alkenyl, $C_{2-20}$ alkynyl, $C_{1-20}$ alkoxy, $C_{2-20}$ alkenyloxy, $C_{5-14}$ aryl, $C_{5-14}$ heteroaryl, $C_{6-14}$ aryloxy, $C_{6-14}$ heteroaryloxy, $C_{1-20}$ alkylcarboxylate, $C_{2-20}$ alkoxycarbonyl, $C_{1-20}$ alkylthio, $C_{1-20}$ alkylsufinyl and $C_{1-20}$ alkylsulfonyl, each optionally substituted with one or more substituents, or $R^1$ and $R^2$ are covalently linked to form a 5- or 6-membered carbocyclic ring that may optionally be part of a bicyclic molecule and which may optionally be substituted with one or more substituents, $R^3$ and $R^{3'}$ are independently 5- or 6-membered aromatic or heteroaromatic rings selected from the group consisting of phenyl, thiophenyl, furanyl, pyridinyl, imidazolinyl, pyranyl, thiopyranyl, pyrrolyl, pyrazolyl, oxazolyl, isoxazolyl, thiazol and isothiazol, that may optionally be substituted with one or more substituents $R^4$, $R^{4'}$ and $R^5$ are independently selected from the group consisting of H, $C_{1-20}$ alkyl, $C_{2-20}$ alkenyl, $C_{2-20}$ alkynyl, $C_{1-20}$ alkoxy, $C_{2-20}$ alkenyloxy, $C_{6-14}$ aryl, $C_{6-14}$ heteroaryl, $C_{6-14}$ aryloxy, $C_{6-14}$ heteroaryloxy, $C_{1-20}$ alkylcarboxylate, $C_{2-20}$ alkoxycarbonyl, $C_{1-20}$ alkylthio, $C_{1-20}$ alkylsulfinyl and $C_{1-20}$ alkylsulfonyl, each optionally substituted with one or more substituents, and no more than three of $R^3$, $R^{3'}$, $R^4$, $R^{4'}$ and $R^5$ are H.

2. The compound of claim 1, wherein L is selected from the group consisting of imidazol-2-ylidenes, dihydroimidazol-2-ylidenes, triazol-5-ylidenes, tetrazol-5-ylidenes, pyrazol-3-ylidenes, benzimidazol-2-ylidenes, oxazol-2-ylidenes, thiazol-2-ylidenes and cyclic alkyl amino carbenes that may optionally be substituted at one or more ring atoms, wherein the substituents at one or both ring atoms neighbouring the carbene C-atom of L are independently selected from $C_{1-6}$ alkyl groups and 5- or 6-membered aromatic or heteroaromatic rings that may optionally be substituted with one or more substituents, and wherein substituents at ring positions of L not neighbouring the carbene C-atom are independently selected from linear or branched $C_{1-6}$ alkyl groups.

3. The compound of claim 1, wherein L is substituted at one or both ring atoms neighbouring the carbene C-atom and optionally at one or more additional ring atoms.

4. The compound of claim 1, wherein L is imidazol-2-ylidene, substituted at one or both N-atoms neighbouring the carbene C-atom and/or at one or both ring C-atoms.

5. The compound of claim 2, wherein both atoms neighbouring the carbene C-atom of L are substituted with phenyl groups that may in turn be substituted with one or more substituents.

6. The compound of claim 1, wherein substituents at ring positions of L not neighbouring the carbene C-atom are independently selected from linear or branched $C_{1-6}$ alkyl groups.

7. The compound of claim 1, wherein one of $R^1$ and $R^2$ is H and the other is a 5- or 6-membered aromatic or heteroaromatic ring selected from the group consisting of phenyl, thiophenyl, furanyl, pyridinyl, imidazolinyl, pyranyl, thiopyranyl, pyrrolyl, pyrazolyl, oxazolyl, isoxazolyl, thiazol and isothiazol, that may optionally be substituted with one or more substituents.

8. The compound of claim 1, wherein $R^1$ and $R^2$ are covalently linked to form a 1H-indene-1-ylidene group, optionally substituted with a phenyl group.

9. The compound of claim 1, wherein $R^4$ and $R^{4'}$ are H and/or wherein $R^5$ is H, phenyl or anthracenyl, optionally substituted with one or more substituents.

10. The compound of claim 1, wherein substituents at $R^3$, $R^{3'}$, $R^4$, $R^{4'}$ and $R^5$ are independently selected from the group consisting of $C_{1-6}$ alkyl, phenyl and $CF_3$.

11. A catalyst for catalysing olefin metathesis reactions comprising a compound of claim 1, wherein the olefin metathesis reaction comprises a reaction selected from ring-closing metathesis, ring-opening metathesis, cross-metathesis, and ring opening metathesis polymerization.

12. The catalyst of claim 11 which is in free form or bound to a support.

13. The compound of claim 5, wherein one of $R^1$ and $R^2$ is H and the other is a 5- or 6-membered aromatic or heteroaromatic ring selected from the group consisting of phenyl, thiophenyl, furanyl, pyridinyl, imidazolinyl, pyranyl, thiopyranyl, pyrrolyl, pyrazolyl, oxazolyl, isoxazolyl, thiazol and isothiazol, that may optionally be substituted with one or more substituents.

14. The compound of claim 6, wherein one of $R^1$ and $R^2$ is H and the other is a 5- or 6-membered aromatic or heteroaromatic ring selected from the group consisting of phenyl, thiophenyl, furanyl, pyridinyl, imidazolinyl, pyranyl, thiopyranyl, pyrrolyl, pyrazolyl, oxazolyl, isoxazolyl, thiazol and isothiazol, that may optionally be substituted with one or more substituents.

15. The compound of claim 9, wherein substituents at $R^3$, $R^{3'}$, $R^4$, $R^{4'}$ and $R^5$ are independently selected from the group consisting of $C_{1-6}$ alkyl, phenyl and $CF_3$.

16. The compound of claim 1, wherein $R^3$ and $R^{3'}$ are phenyl, optionally substituted with one or more substituents.

17. A method for catalysing olefin metathesis reactions comprising combining a compound of claim 1 with an olefin, wherein the olefin metathesis reaction comprises a reaction selected from ring-closing metathesis, ring-opening metathesis, cross-metathesis, and ring opening metathesis polymerization.

18. The method of claim 17, wherein the compound of claim 1 is capable of stereoselectively generating disubstituted olefinic products.

19. The method of claim 17, wherein the compound of claim 1 is in free form or bound to a support.

\* \* \* \* \*

UNITED STATES PATENT AND TRADEMARK OFFICE
CERTIFICATE OF CORRECTION

PATENT NO. : 10,265,691 B2
APPLICATION NO. : 15/742668
DATED : April 23, 2019
INVENTOR(S) : Vidar R. Jensen et al.

It is certified that error appears in the above-identified patent and that said Letters Patent is hereby corrected as shown below:

In the Claims

Column 36, Line 26-Column 37, Line 4, (approx.), should read:
1. A compound having the general Formula (I):

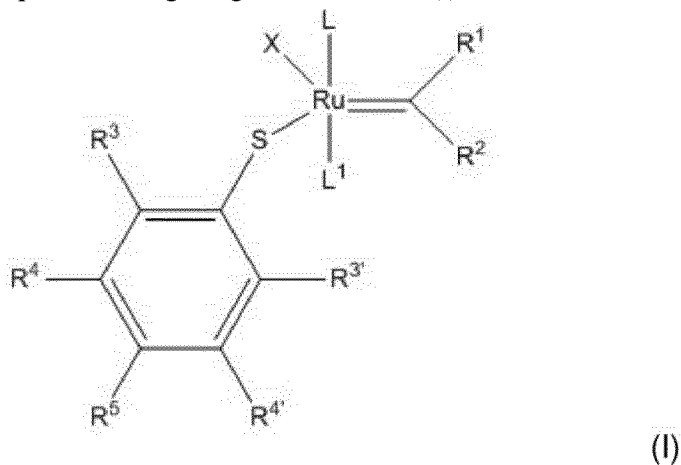

(I)

wherein
L    is an N-heterocyclic carbene ligand,
$L^1$    is pyridine, that may optionally be substituted with one or more substituents,
X    is halide, -NCO, -CN, -CNO, -NCS, or $-N_3$,
$R^1$ and $R^2$ are independently selected from the group consisting of H, $C_{1-20}$ alkyl, $C_{2-20}$ alkenyl, $C_{2-20}$ alkynyl, $C_{1-20}$ alkoxy, $C_{2-20}$ alkenyloxy, $C_{5-14}$ aryl, $C_{5-14}$ heteroaryl, $C_{6-14}$ aryloxy, $C_{6-14}$ heteroaryloxy, $C_{1-20}$ alkylcarboxylate, $C_{2-20}$ alkoxycarbonyl, $C_{1-20}$ alkylthio, $C_{1-20}$ alkylsufinyl and $C_{1-20}$ alkylsulfonyl, each optionally substituted with one or more substituents,
or $R^1$ and $R^2$ are covalently linked to form a 5- or 6-membered carbocyclic ring that may optionally be part of a bicyclic molecule and which may optionally be substituted with one or more substituents, Signed and Sealed this
Fourteenth Day of April, 2020

Andrei Iancu
*Director of the United States Patent and Trademark Office*

$R^3$ and $R^{3'}$ are independently 5- or 6-membered aromatic or heteroaromatic rings selected from the group consisting of phenyl, thiophenyl, furanyl, pyridinyl, imidazolinyl, pyranyl, thiopyranyl, pyrrolyl, pyrazolyl, oxazolyl, isoxazolyl, thiazol and isothiazol, that may optionally be substituted with one or more substituents $R^4$, $R^{4'}$ and $R^5$ are independently selected from the group consisting of H, $C_{1-20}$ alkyl, $C_{2-20}$ alkenyl, $C_{2-20}$ alkynyl, $C_{1-20}$ alkoxy, $C_{2-20}$ alkenyloxy, $C_{6-14}$ aryl, $C_{6-14}$ heteroaryl, $C_{6-14}$ aryloxy, $C_{6-14}$ heteroaryloxy, $C_{1-20}$ alkylcarboxylate, $C_{2-20}$ alkoxycarbonyl, $C_{1-20}$ alkylthio, $C_{1-20}$ alkylsulfinyl and $C_{1-20}$ alkylsulfonyl, each optionally substituted with one or more substituents, and no more than three of $R^3$, $R^{3'}$, $R^4$, $R^{4'}$ and $R^5$ are H.